United States Patent
North

(10) Patent No.: US 9,242,955 B2
(45) Date of Patent: Jan. 26, 2016

(54) SYNTHESIS OF CYCLIC CARBONATES

(75) Inventor: Michael North, Newcastle Upon Tyne (GB)

(73) Assignee: University of York, York (GB)

( * ) Notice: Subject to any disclaimer, the term of this patent is extended or adjusted under 35 U.S.C. 154(b) by 855 days.

(21) Appl. No.: 12/597,417

(22) PCT Filed: Apr. 25, 2008

(86) PCT No.: PCT/GB2008/001485
§ 371 (c)(1),
(2), (4) Date: Oct. 23, 2009

(87) PCT Pub. No.: WO2008/132474
PCT Pub. Date: Nov. 6, 2008

(65) Prior Publication Data
US 2010/0130752 A1    May 27, 2010

(30) Foreign Application Priority Data
Apr. 25, 2007 (GB) .................................. 0708016.1

(51) Int. Cl.
  *C07D 317/12*  (2006.01)
  *C07D 317/14*  (2006.01)
  *C07F 5/06*    (2006.01)

(52) U.S. Cl.
CPC .............. *C07D 317/12* (2013.01); *C07F 5/069* (2013.01)

(58) Field of Classification Search
CPC ............................ C07D 317/12; C07D 317/14
USPC ....................................... 544/64; 549/229, 230
See application file for complete search history.

(56) References Cited

U.S. PATENT DOCUMENTS

| 2,773,070 | A | 12/1956 | Lichtenwalter et al. |
| 6,521,561 | B1 * | 2/2003 | Jacobsen et al. ............... 502/162 |
| 2008/0214386 | A1 | 9/2008 | Takahashi et al. |
| 2013/0317237 | A1 | 11/2013 | North |

FOREIGN PATENT DOCUMENTS

| CN | 1789258 | | 6/2006 |
| CN | 1796384 | A | 7/2006 |
| CN | 101020747 | | 8/2007 |
| EP | 1 970 199 | A1 | 9/2008 |
| JP | 58222079 | A | 12/1983 |
| JP | 02047134 | A | 2/1990 |
| JP | 2005-202022 | A | 8/1993 |
| JP | 2001 003043 | A | 1/2001 |
| JP | 2001-129397 | | 5/2001 |
| JP | 2005-254068 | A | 9/2005 |
| SK | 0284530 | B6 | 6/2005 |
| WO | 03 029325 | A1 | 4/2003 |

| WO | 2005 084801 | A1 | 9/2005 |
| WO | 2006 032716 | A1 | 3/2006 |
| WO | WO2008/132474 | | 11/2008 |

OTHER PUBLICATIONS

Taylor, "Enantioselective Michael Additions to .alpha.,.beta.-Unsaturated Imides Catalyzed by a Salen-Al Complex." Journal of the American Chemical Society, 2003 125(37), 11204-11205.*
Melèndez, Jaisiel, et al: "Synthesis of cyclic carbonates from atmospheric pressure carbon dioxide using exceptionally active aluminum (salen) complexes as catalysts" European Journal of Inorganic Chemistry, vol. 2007, No. 21, 2007, pp. 3323-3326, XP00252661, Wiley-VCH Verlag GmbH & Co., KGaA, Weinheim.
Zhang, Xiang, et al.: "Intramolecularly two-centered cooperation catalysis for the synthesis of cyclic carbonates from CO2 and epoxides" Tetrahedron Letters, No. 49 (2008) pp. 6589-6592, Elsevier Ltd.
Sujith S., et al.: "A highly active and recyclable catalytic system for CO2/Propylene Oxide Copolymerization" Agnew Chem. Int. Ed., 2008, vol. 47, pp. 7306-7309, Wiley-VCH Verlag GmbH & Co., KGaA, Weinheim.
Broadwith: "Waste CO2 turned into useful molecules" Chemistry World, Dec. 2009, p. 29, Royal Society of Chemistry, UK.
Clegg, William, et al.: "Cyclic carbonate synthesis catalysed by bimetallic aluminium-salen complexes" Chem. Eur. J., 2010, vol. 16, pp. 6828-6843, Wiley-VCH Verlag GmbH & Co., KGaA, Weinheim.
Melèndez, Jaisiel, et al: "One-component catalysis for cyclic carbonate synthesis" Chem. Commun., 2009, pp. 2577-2579, The Royal Society of Chemistry, UK.
Metcalfe, Ian S., et al.: "An integrated approach to energy and chemicals production" Energy Environ. Sci., 2010, vol. 3, pp. 212-215, The Royal Society of Chemistry, UK.
North, Michael, et al.: "Mechanism of Cyclic Carbonate Synthesis from Epoxides and CO2" Agneew Chem. Int. Ed., 2009, vol. 48, pp. 2946-2948, Wiley-VCH Verlag GmbH & Co., KGaA, Weinheim.

(Continued)

*Primary Examiner* — David K O Dell
(74) *Attorney, Agent, or Firm* — Steptoe & Johnson LLP

(57) ABSTRACT

A process for the production of cyclic carbonates comprising contacting an epoxide with carbon dioxide in the presence of a dimeric aluminum(salen) catalyst, and a co-catalyst capable of supplying $Y^-$, where Y is selected from Cl, Br and I, where the dimeric aluminum(salen) catalyst is of formula I:

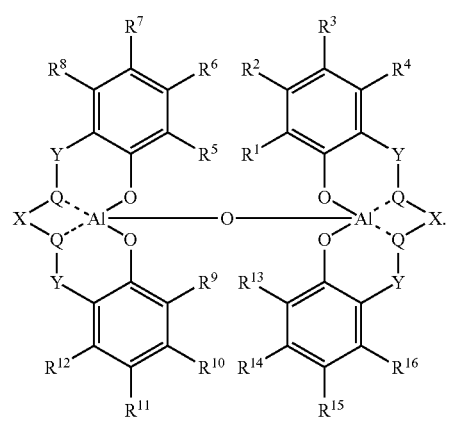

7 Claims, No Drawings

(56) References Cited

OTHER PUBLICATIONS

North, Michael, et al.: "A Gas-Phase Flow Reactor for Ethylene Carbonate Synthesis from Waste Carbon Dioxide" Chem. Eur. J., 2009, vol. 15, pp. 11454-11457, Wiley-VCH Verlag GmbH & Co., KGaA, Weinheim.

North, Michael, et al.: "Synthesis of cyclic carbonates from epoxides and CO2" Green Chemistry, 2010, DOI 10, 1039_c0GC00065e, The Royal Society of Chemistry, UK.

North, Michael, et al."Aluminium(salen) and Tetrabutylammonium Bromide CatalysedSynthesis of Cyclic Di- and Trithiocarbonates from Epoxides and Carbon Disulfide" SYNLETT, 2010, No. 4, pp. 0623-0627, Georg Thieme Verlag Stuttgart, New York.

Vanderwal, Christopher D., et al.: "Enantioselective Formal Hydration of α,β-Unsaturated Imides by Al-Catalyzed Conjugate Addition of Oxime Nucleophiles" J.Am. Chem. Soc. 2004, vol. 126, 14724-14725, American Chemical Society.

Larrow, Jay F., et al.: "A Practical Method for the Large-Scale Preparation of [N,N'-Bis(3,5-di-tert-buty lsalicylidene)-1,2-cyclohexanediaminato(2-) ]manganese (III) Chloride, a Highly Enantioselective Epoxidation Catalyst" J. Org. Chem. 1994, vol. 59, 1939-1942, American Chemical Society.

Shen, Yu-Mei, et al.: "Chemical Fixation of Carbon Dioxide Catalyzed by Binaphthyldiamino Zn, Cu, and Co Salen-Type Complexes" J. Org. Chem. 2003, vol. 68, 1559-1562, American Chemical Society.

Wang, Yuhong et al.: "Five-coordinate organoaluminum acetylides and crystal structure of the hydrosylate, [Salophen(tBu)Al]2O", J. of Organic Chemistry, 2004, vol. 689, 759-765.

Matsumoto, Kazuhiro, et al.: "Catalytic Enantioselective Epoxidation of Unfunctionalized Olefins: Utility of a Ti(Oi-Pr)4-Salan-H2O2 System," Synlett 2006, vol. 20, 3545-3547, Georg Thieme Verlag Stuttgart, New York.

Shitama, Hiroaki, et al.: "Asymmetric epoxidation using aqueous hydrogen peroxide as oxidant: bio-inspired construction of pentacoordinated Mn-salen complexes and their catalysis," Tetrahedron Letters 2006, vol. 47, 3203-3207, Elsevier Ltd.

Gandelman, Mark, et al.: "Highly Enantioselective Catalytic Conjugate Addition of N-Heterocycles to α,β-Unsaturated Ketones and Imides," Chem. Int. Ed. 2005, vol. 44, 2393-2397, Wiley-VCH Verlag GmbH & Co. KGaC, Weinheim.

Kureshy, R.I., et al.: "Environment friendly protocol for enantioselective epoxidation of non-functionalized alkenes catalyzed by recyclable homochiral dimeric Mn(III) salen complexes with hydrogen peroxide and UHP adduct as oxidants," Catalysis Letters, 2006, vol. 107, Nos. 1-2, Springer Science + Business Media, Inc.

Nomura, Nobuyoshi, et al.: "Stereoselective Ring-Opening Polymerization of a Racemic Lactide by Using Achiral Salen- and Homosalen-Aluminum Complexes," Chem Eur. J., 2007, vol. 13, 4433-4451, Wiley-VCH Verlag GmbH & Co. KGaA, Weinheim.

Gurian, Patrick L., et al.: "Aluminium Complexes of N,N,'-Ethylenebis(salicylideneimine)-( H2salen). X-Ray Crystal Structures of [{Al(salen)}, 2(u-O)].MeCn and [Al(OC6H2Me3,-2,4,6)(salen)]," J. Chem. Soc., Dalton Trans. (Inorganic), 1991, vol. 6, 1449-1456.

Attwood, David, et al.: "Group 13 Compounds Incorporating Salen Ligands," Chem. Rev. 2001, vol. 101, 37-52, American Chemical Society.

Gisch, Nicolas, et al.: "Enzymatically Activated cycloSal-d4T-monophosphates: The Third Generation of cycloSal-Pronucleotides," J. Med. Chem. 2007, vol. 50, 1658-1667, American Chemical Society.

Rutherford, Drew, et al.: "Five-Coordinate Aluminum Amides," Organometallics 1996, vol. 15, 4417-4422, American Chemical Society.

Pervaiz, Muhammad, et al.: "Carbon storage potential in natural fiber composites," Resources, Conservation and Recycling 2003, vol. 39, 325-340, Elsevier Science B.V.

Irie, Ryo, et al.: "Enantioselective Expoxidation of Chromene Derivatives using Hydrogen peroxide as a Terminal Oxidant," Synlett 1994, 255-256 (Japan).

Achard, Theirry, R.J., et al.: "Asymmetric Catalysis of Carbon—Carbon Bond-Forming Reactions Using Metal(salen) Complexes," Synlett 2005, No. 12, 1828-1847, Georg Thieme Verlag Stuttgart, New York.

Iida, Takehiko, et al.: "Cyclocondensation of Oxalyl Chloride with 1,2-Glycols," Tetrahedron, 1993, vol. 49, No. 46, 10511-10530, Ferguson Pres, Ltd. UK.

North, Michael, "Synthesis and applications of non-racemic cyanohydrins," Tetrahedron: Asymmetry 2003, vol. 14 147-176, Elsevier Science Ltd.

Dzugan, Sharlene J., et al.: "Factors Affecting Al—C Bond Reactivity of Tetradentate Schiff-Base Organoaluminum Complexes," Inorg. Chem 1986, vol. 25, 2858-2864, American Chemical Society.

Sammis, Glenn M., et al.: "Highly Enantioselective, Catalytic Conjugate Addition of Cyanide to α,β-Unsaturated Imides," J. Am. Chem. Soc. 2003, vol. 125, 4442-4443, American Chemical Society.

Taylor, Mark S., et al.: "Enantioselective Michael additions to α,β-unsaturated imides catalyzed by a Salen-Al complex," Sep. 2003 vol. 125, Issue 37, 11204-11205.

Nakano, Koji, et al.: "Selective Formation of Polycarbonate over Cyclic Carbonate: Copolymerization of Epoxides with Carbon Dioxide Catalyzed by a Cobalt(III) Complex with a Piperidinium End-Capping Arm," Chem. Int. Ed. 2006, vol. 45, 7274-7277, Wiley-VCH Verlag GmbH & Co. KGaA, Weinheim.

Maroto, A., et al.: "Relationship between surface properties of PtSn±SiO2 catalysts and their catalytic performance for the CO2 and propylene reaction to yield hydroxybutanoic acid," Appl. Organometal. Chem. 2000, vol. 14, 783-788, John Wiley & Sons, Ltd.

Balskus, Emily P., et al.: "A,β-Unsaturated β-Silyl Imide Substrates for Catalytic, Enantioselective Conjugate Additions: A Total Synthesis of (+)-Lactacystin and the Discovery of a New Proteasome Inhibitor," J.. Am. Chem. Soc. 2006, vol. 128, 6810-6812, American Chemical Society.

Sung-Suh, Hyung Mi, et al.: "Photoinduced activation of CO2 by rhenium complexes encapsulated in molecular sieves," Appl. Organometal. Chem. 2000 vol. 14, 826-830, John Wiley & Sons, Ltd.

Kosugi, Yoshio, et al.: "Carboxylation of alkali metal phenoxide with carbon dioxide at terrestrial temperature," Appl. Organometal. Chem. 2000, vol. 14, 841-843, John Wiley & Sons, Ltd.

Ballivet-Tkatchenko, Danielle, et al.: "Electrocatalytic reduction of CO2 for the selective carboxylation of olefins," Appl. Organometal. Chem., 2000, vol. 14, 847-849, John Wiley & Sons, Ltd.

Tanaka, Koji, et al.: "Selective formation of ketones by electrochemical reduction of CO2 catalyzed by ruthenium complexes," Appl. Organometal. Chem., 2000, vol. 14, 863-866, John Wiley & Sons, Ltd.

Styring, Peter, et al.: "A polymer-supported nickel(II) catalyst for room temperature Tamao-Kumada-Corriu coupling reactions," Catalysis Letters 2001, vol. 77, No. 4, Plenum Publishing Corporation.

Molnar, Ferenc, et al.: Multisite Catalysis: A Mechanistic Study of β-Lactone Synthesis from Epoxides and CO-Insights into a Difficult Case of Homogeneous Catalysis, Chem. Eur. J., 2003, vol. 9, No. 6, 1273-1280, Wiley-VCH Verlag GmbH & Co. KGaA, Weinheim.

Phan, Nam, T.S., et al.: "Solid-supported cross-coupling catalysts derived from homogeneous nickel and palladium coordination complexes," Appl. Organometal Chem., 2000, vol. 14, 794-798, The Royal Society of Chemistry, UK.

Shen, Yu-Mei, "Chemical Fixation of Carbon Dioxide Co-Catalyzed by a Combination of Schiff Bases or Phenols and Organic Bases," Eur. J. Org. Chem. 2004, 3080-3089, Wiley-VCH Verlag GmbH & co. KGaA, Weinheim.

Braunstein, Pierre, et al.: "Carbon Dioxide Activation and Catalytic Lactone Synthesis by Telomerization of Butadiene and CO2," J. Am. Chem. Soc., 1988, vol. 110, 3207-3212, American Chemical Society.

(56) References Cited

OTHER PUBLICATIONS

Tsuda, Tetsuo, et al.: "Nickel(0)-Catalyzed Alternating Copolymerization of Carbon Dioxide with Diynes to Poly (2-pyrones)," J. Am. Chem. Soc. 1992, vol. 114, 1498-1499, American Chemical Society.

Hoffman, William A., III: "Convenient Preparation of Carbonates from Alcohols and Carbon Dioxide," J. Org. Chem. 1982, vol. 47, 5209-5210, American Chemical Society.

Tsuda, Tetsuo, et al.: "Nickel(O)-Catalyzed Cycloaddition of Diynes and Carbon Dioxide to Bicyclic α-Pyrones," J. Org. Chem. 1988, vol. 53, 3140-3145, American Chemical Society.

Shi, Min, et al.: "Transition-Metal-Catalyzed Reactions of Propargylamine with Carbon Dioxide and Carbon Disulfide," J. Org. Chem. 2002, vol. 67, 16-21, American Chemical Society.

Lefeber, C., et al.: "Regioselektive Reaktionen der fremdligandfreien Titanocen-Alkin-Komplexe Cp,Ti( RC,SiMe,) (R = Me,3, Ph, 1Bu, nBu)," J. Organometallic Chemistry, 1995 vol. 501, 179-188, Elsevier Science S.A.

Tsuda, Tetsuo, et al.: "Nickel(0)-Catalyzed Cycloaddition Copolymerization of Ether Diynes with Carbon Dioxide to Poly(2-pyrone)s," Macromolecules 1996, vol. 28, 1356-1359, American Chemical Society.

McGee, William, et al.: "Palladium-Catalyzed Generation of 0-Allylic Urethanes and Carbonates from Amines/Alcohols, Carbon Dioxide, and Allylic Chlorides," Organometallics 1993, vol. 12, 1429-1433, American Chemical Society.

Bartoli, Giuseppe, et al.: "Direct Catalytic Synthesis of Enantiopure 5-Substituted Oxazolidinones from Racemic Terminal Epoxides," Organic Letters 2005, vol. 7, No. 10, 1983-1985, American Chemical Society.

Mizojiri, Ryo, et al.: Regioselectivity in the nickel-catalysed coupling of cyclic carbonates of but-3-ene-1,2-diols with organoborates, J. Chem. Soc. Perkin Trans. 1995, 2073-2075.

Gholamkhass, Bobak, et al.: "Architecture of Supramolecular Metal Complexes for Photocatalytic CO2 Reduction: Ruthenium—Rhenium Bi- and Tetranuclear Complexes," Inorganic Chemistry, 2005, vol. 44, No. 7, American Chemical Society.

Takavec, Thomas N., et al.: "Regioselectivity in nickel(0) catalyzed cycloadditions of carbon dioxide with diynes," Tetrahedron 60, 2004, 7431-7437, Elsevier Ltd. UK.

Phan, Nam T.S., et al.: "Polymer-supported palladium catalysed Suzuki-Miyaura reactions in batch and a mini-continuous flow reactor system," Tetrahedron 61, 2005, 12065-12073, Elsevier Science Ltd. UK.

Matsumoto, Kazutsugu, et al.: "Enzyme-Mediated Enantioselective Hydrolysis of Cyclic Carbonates," Tetrahedron Letters, 1995, vol. 36, No. 36, 6499-6502, Elsevier Science Ltd. UK.

Chang, Han-Ting, et al.: "A Practical Route to Enantiopure 1,2-Aminoalcohols." Tetrahedron Letters, 1996, vol. 37, No. 19, 3219-3222, Elsevier Science Ltd. UK.

Schultze, Lisa M., et al.: "Practical Synthesis of the anti-HIV Drug, PMPA," Tetrahedron Letters 39, 1998, 1853-1856, Elsevier Science Ltd. UK.

S. Jegham, et al.: "Use of Chiral Glycerol 2,3-Carbonate in the Synthesis of 3-Aryl-2-oxazolidinones," Tetrahedron Letters 39, 1998, 4453-4454, Elsevier Science Ltd. UK.

Phan, Nam, T.S., et al.: "A polymer-supported salen-type palladium complex as a catalyst for the Suzuki-Miyaura cross-coupling reaction," Tetrahedron Letters 45, 2004, 7915-7919, Elsevier Science Ltd. UK.

Taylor, Mark S., et al., "Highly Enantioselective Conjugate Additions to r,ä-Unsaturated Ketones Catalyzed by a (Salen)Al Complex", JACS Articles, Published on Web Jan. 6, 2005.

Maggi, Raimondo, et al.: "Synthesis of oxazolidinones in supercritical CO2 under heterogeneous catalysis", Science Direct, Tetrahedron Letters 48 (2007) 2131-2134.

Saito, Mashairo, et al., "Advances in joint research between NIRE and RITE for developing a novel technology for methanol synthesis from CO2 and H2", Applied Organometallic Chemistry Appl. Organometal. Chem. 14, 763-772 (2000).

Nam, Sang-Sung, et al., "Effect of lanthanum loading in Fe±K/La±Al2O3 catalysts for CO2 hydrogenation to hydrocarbons", Applied Organometallic Chemistry Appl. Organometal. Chem. 14, 794-798 (2000).

Ushikoshi, Kenji, et al., "Methanol synthesis from CO2 and H2 in a bench-scale test plant", Applied Organometallic Chemistry Appl. Organometal. Chem. 14, 819-825 (2000).

Ando, Hisanori, et al., "Active phase of iron catalyst for alcohol formation in hydrogenation of carbon oxides", Applied Organometallic Chemistry Appl. Organometal. Chem. 14, 831-835 (2000).

Kusama, Hitoshi, et al., "Alcohol synthesis by catalytic hydrogenation of CO2 over Rh±Co/SiO2", Applied Organometallic Chemistry Appl. Organometal. Chem. 14, 836-840 (2000).

Joo, Ferenc, et al., "NOTE Homogeneous hydrogenation of aqueous hydrogen carbonate to formate under mild conditions with water soluble rhodium(I)± and ruthenium(II)±phosphine catalysts", Applied Organometallic Chemistry Appl. Organometal. Chem. 14, 857-859 (2000).

Shen, Yu-Mei, et al., "Phenol and Organic Bases Co-Catalyzed Chemical Fixation of Carbon Dioxide with Terminal Epoxides to Form Cyclic Carbonates", State Key Laboratory of Organometallic Chemistry, Shanghai Institute of Organic Chemistry, Chinese Academy of Sciences, 354 Fenglin Lu, Shanghai 200032, P. R. China.

Kim, Hoon Sik, et al., Isolation of a Pyridinium Alkoxy Ion Bridged Dimeric Zinc complex for the Coupling Reactions of CO2 and Epoxides, Angew. Chem. Int. Ed. 2000, 39, No. 22.

Aresta, Michele, et al.; "Direct synthesis of organic carbonates by oxidative carboxylation of ole® ns catalyzed by metal oxides: developing green chemistry based on carbon dioxide", Applied Organometallic Chemistry Appl. Organometal. Chem. 14, 799-802 (2000).

Sun, Jianmin, et al., "Direct oxidative carboxylation of styrene to styrene carbonate in the presence of ionic liquids", Science Direct, Catalysis Communications 5 (2004) 83-87.

Vieville, C., et al., "Synthesis of glycerol carbonate by direct carbonatation of glycerol in supercritical CO2 in the presence of zeolites and ion exchange resins", Catalysis Letters 56 (1998) 245-247.

Srivastava, R., et al., "Synthesis of polycarbonate precursors over titanosilicate molecular sieves", Catalysis Letters vol. 91, Nos. 1-2, Nov. 2003 (# 2003).

Sun, Jianmin, et al., "One-pot synthesis of styrene carbonate from styrene in tetrabutylammonium bromide", Science Direct, Catalysis Today 93-95 (2004) 383-388.

Dibenedetto, Angela, et al., "Synthesis of cyclic carbonates from epoxides: Use of reticular oxygen of Al2O3 or Al2O3-supported CeOx for the selective epoxidation of propene", Science Direct, Catalysis Today 115 (2006) 117-123.

Kisch, Horst, et al., "Bifunktionelle Katalysatoren zur Synthese cyclischer Carbonate aus Oxiranen und Kohlendioxid"; Chem. Ber. 119. 1095-1100 (1986).

Tominaga, Ken-Ichi, et al., "Ethylene Oxide-mediated Reduction of CO2 to CO and Ethylene Glycol catalysed by Ruthenium Complexes", J. Chem. Soc., Chem. Commun., 1995.

Tascedda, Patricia, et al., "Novel Electrochemical Reactivity of Ni(cyclam)Br2: Catalytic Carbon Dioxide Incorporation into Epoxides", J. Chem. Soc., Chem. Commun., 1995.

Yano, Takashi, et al., "Magnesium oxide-catalysed reaction of carbon dioxide with an epoxide with retention of stereochemistry", pp. 1129-1130, Chem. Commun., 1997.

Kawanami, Hajime, et al., "Chemical fixation of carbon dioxide to styrene carbonate under supercritical conditions with DMF in the absence of any additional catalysts", Chem. Commun., 2000, 2089-2090.

Yang, Hongzhou, et al., "Electrochemical activation of carbon dioxide in ionic liquid: synthesis of cyclic carbonates at mild reaction conditions", Chem. Commun., 2002, 274-275.

(56) References Cited

OTHER PUBLICATIONS

Kawanami, Hajime, et al., "A rapid and effective synthesis of propylene carbonate using a supercritical CO2-ionic liquid system", Chem. Commun., 2003, 896-897.

Mori, Kohsuke, et al., "A single-site hydroxyapatite-bound zinc catalyst for highly efficient chemical fixation of carbon dioxide with epoxides", Chem. Commun., 2005, 3331-3333.

Takahashi, Toshikazu, et al., "Synergistic hybrid catalyst for cyclic carbonate synthesis: Remarkable acceleration caused by immobilization of homogeneous catalyst on silica", Chem. Commun., 2006, 1664-1666.

Kim, Hoon Sik, et al., "New Mechanistic Insight into the Coupling Reactions of CO2 and Epoxides in the Presence of Zinc Complexes", Chem. Eur. J. 2003, 9, No. 3.

Man, Lok Man, et al., "Synthesis of Heterobimetallic Ru☐Mn Complexes and the Coupling Reactions of Epoxides with Carbon Dioxide Catalyzed by these Complexes", Chem. Eur. J. 2006, 12, 1004-1015.

Takata, Toshikazu, et al., "Synthesis of Calix[4]arene and Porphyrin Tethering Four Chiral Five-Membered Cyclic Carbonates", Enantiomer, vol. 7, pp. 129-132.

Aresta, Michele, et al., "Unique Evidence for a RhIII to RhI Reduction by Deoxygenation of a Carbonate Moiety to CO2 by an Out-of-Sphere Phosphane", Eur. J. Inorg. Chem. 2001, 180121806.

Solladie-Cavallo, Arlette, et al., "A Mild Stereo- and Enantiospecific Conversion of 2,3-Diaryl-Substituted Oxiranes into 2,2-Dimethyl-1,3-Dioxolanes by an Acetone/Amberlyst 15 System", Eur. J. Org. Chem. 2006, 3007-3011.

Sako, Takeshi, et al., "Cycloaddition of Oxirane Group with Carbon Dioxide in the Supercritical Homogeneous State", Ind. Eng. Chem. Res. 2002, 41, 5353-5358.

Aida, Takuzo, et al., "Activation of Carbon Dioxide with Aluminum Porphyrin and Reaction with Epoxide. Studies on (Tetraphenylporphinato)aluminum Alkoxide Having a Long Oxyalkylene Chain as the Alkoxide Group", J. Am. Chem. Soc. 1983, 105, 1304-1309.

Trost, Barry M., et al., Palladium-Mediated Vicinal Cleavage of Allyl Epoxides with Retention of Stereochemistry: A Cis Hydroxylation Equivalent, J. Am. Chem. Soc. 1985, 107, 6123-6124.

Myers, Andrew G., "Stereochemical Assignment of Neocarzinostatin Chromophore. Structures of Neocarzinostatin Chromophore-Methyl Thioglycolate Adductst", J. Am. Chem. Soc. 1988, 110, 7212-7214.

Sugimoto, Hiroshi, et al., "Photoresponsive Molecular Switch to Control Chemical Fixation of CO2", J. Am. Chem. Soc. 1999, 121, 2325-2326.

Yamaguchi, Kazuya, et al., "Mg—Al Mixed Oxides as Highly Active Acid-Base Catalysts for Cycloaddition of Carbon Dioxide to Epoxides", J. Am. Chem. Soc. 1999, 121, 4526-4527.

Paddock, Robert L., et al., "Chemical CO2 Fixation: Cr(III) Salen Complexes as Highly Efficient Catalysts for the Coupling of CO2 and Epoxides", J. Am. Chem. Soc. 2001, 123, 11498-11499.

Shi, Feng, et al., "From CO Oxidation to CO2 Activation: An Unexpected Catalytic Activity of Polymer-Supported Nanogold", JACS Communications, Published on Web Mar. 4, 2005.

Doll, Kenneth M., et al., "Synthesis of Carbonated Fatty Methyl Esters Using Supercritical Carbon Dioxide", J. Agric. Food Chem. 2005, 53, 9608-9614.

Tu, Mai, et al., "Cycloaddition of CO2 to Epoxides over Solid Base Catalysts", Journal of Catalysis 199, 85-91 (2001).

Kim, Hoon Sik, et al., "Well-Defined Highly Active Heterogeneous Catalyst System for the Coupling Reactions of Carbon Dioxide and Epoxides", Journal of Catalysis 205, 226-229 (2002).

Yasuda, Hiroyuki, et al., "Cyclic Carbonate Synthesis from Supercritical Carbon Dioxide and Epoxide over Lanthanide Oxychloride", Journal of Catalysis 209, 547-550 (2002).

Sun, Jianmin, et al., "A direct synthesis of styrene carbonate from styrene with the Au/SiO2—ZnBr2/Bu4NBr catalyst system", Science Direct, Journal of Catalysis 230 (2005) 398-405.

Yasuda, Hiroyuki, et al., "Efficient synthesis of cyclic carbonate from carbon dioxide catalyzed by polyoxometalate: the remarkable effects of metal substitution", Science Direct, Journal of Catalysis 233 (2005) 119-122.

Srivastava, R., et al., "CO2 activation and synthesis of cyclic carbonates and alkyl/aryl carbamates over adenine-modified Ti-SBA-15 solid catalysts", Science Direct, Journal of Catalysis 233 (2005) 1-15.

Aresta, Michele, et al., "Carbon dioxide as building block for the synthesis of organic carbonates Behavior of homogeneous and heterogeneous catalysts in the oxidative carboxylation of olefins", Journal of Molecular Catalysis A: Chemical 182-183 (2002) 399-409.

Nomura, Ryoki, et al., "Synthesis of Cyclic Carbonates from Carbon Dioxide and Epoxides in the Presence of Organoantimony Compounds as Novel Catalysts", J. Org. Chsm. 1980, 45, 3735-3738.

Kihara, Nobuhiro, et al., "Catalytic Activity of Various Salts in the Reaction of 2,3-Epoxypropyl Phenyl Ether and Carbon Dioxide under Atmospheric Pressure", J. Org. Chem. 1993, 58, 6198-6202.

Kihara, Nobuhiro, et al., "Preparation of 1,3-Oxathiolane-2-thionebsy the Reaction of Oxirane and Carbon Disulfide", J. Org. Chem. 1996, 60, 473-475.

Kruper, William J., et al., "Catalytic Formation of Cyclic Carbonates from Epoxides and C02 with Chromium Metalloporphyrinates", J. Org. Chem. 1996, 60, 725-727.

Hu, Shaojing, et al., "An Efficient Synthesis of (+)-exo-Brevicomin via Chloroallylboration", J. Org. Chem. 1999, 64, 2524-2526.

Huang, Jin-Wen, et al., "Chemical Fixation of Carbon Dioxide by NaI/PPh3/PhOH", J. Org. Chem. 2003, 68, 6705-6709.

Jiang, Jia-Li, et al., "Re(CO)5Br-Catalyzed Coupling of Epoxides with CO2 Affording Cyclic Carbonates under Solvent-Free Conditions", J. Org. Chem. 2005, 70, 381-383.

Kim, Yong Jin, et al., "Tetrahaloindate(III)-Based Ionic Liquids in the Coupling Reaction of Carbon Dioxide and Epoxides to Generate Cyclic Carbonates: H-Bonding and Mechanistic Studies", J. Org. Chem. 2005, 70, 7882-7891.

Sit, Wing Nga, et al., "Coupling Reactions of CO2 with Neat Epoxides Catalyzed by PPN Salts to Yield Cyclic Carbonates", J. Org. Chem. 2005, 70, 8583-8586.

Lu, Xiao-Bing, et al., "Aluminum phthalocyanine complex covalently bonded to MCM-41 silica as heterogeneous catalyst for the synthesis of cyclic carbonates", Journal of Molecular Catalysis A: Chemical 186 (2002) 33-42.

Doskocil, Eric J., et al., "UV-Vis Spectroscopy of Iodine Adsorbed on Alkali-Metal-Modified Zeolite Catalysts for Addition of Carbon Dioxide to Ethylene Oxide", J. Phys. Chem. B 1999, 103, 6277-6282.

Peng, Jiajian, et al., "Cycloaddition of carbon dioxide to propylene oxide catalyzed by ionic liquids", New J. Chem., 2001, 25, 639-641.

Xie, Haibo, et al., "The effective synthesis of propylene carbonate catalyzed by silica-supported hexaalkylguanidinium chloride", New J. Chem., 2005, 29, 1199-1203.

Calo, Vincenzo, et al., "Cyclic Carbonate Formation from Carbon Dioxide and Oxiranes in Tetrabutylammonium Halides as Solvents and Catalysts", American Chemical Society, Published on Web Jun. 29, 2002.

Berkessel, Albrecht, et al., "Catalytic Asymmetric Addition of Carbon Dioxide to Propylene Oxide with Unprecedented Enantioselectivity", American Chemical Society, Published on Web Aug. 26, 2006.

Zhao, Tiansheng, et al., "Cydoaddition between propylene oxide and CO2 over metal oxide supported KI", Phys. Chem. Chem. Phys., 1999, 1, 3047-3051.

Kasuga, Kuninobu, et al., "Cycloaddition of Carbon Dioxide to Propylene Oxide Catalysed by Tetra-t-Butylphthalocyaninatoaluminium(III) Chloride", Polyhedron vol. 15, No. 1, pp. 69-72, 1996.

(56) References Cited

OTHER PUBLICATIONS

Sakharov, A.M., et al., "Copolymerization of propylene oxide with carbon dioxide catalyzed by zinc adipate", Russian Chemical Bulletin, International Edition, vol. 51, No. 8, pp. 1451-1454, Aug. 2002.

Lermontov, S.A., et al., "8-Hydroxyquinolates of trivalent metals as new catalysts for the reaction of CO2 with epoxides", Russian Chemical Bulletin, International Edition, vol. 51, No. 5, pp. 836-838, May 2002.

Rybina, G.V., et al., "Synthesis of Cyclic Organic Carbonates from C3☐C16 Epoxides", Russian Journal of Applied Chemistry, vol. 76, No. 5, 2003, pp. 842-843. Translated from Zhurnal Prikladnoi Khimii, vol. 76, No. 5, 2003, pp. 870-871.

Lermontov, S.A., et al., "Aluminum 8-Hydroxyquinolate, A New Catalyst for CO2 Reactions with Epoxides", Russian Journal of General Chemistry, vol. 72, No. 9, 2002, pp. 1492-1493. Translated from Zhurnal Obshchei Khimii, vol. 72, No. 9, 2002, pp. 1581-1582.

Zaitseva, V.V., et al., "Synthesis and Structure of 8-Methyl-2-methylene-1,4,6,9-tetraoxaspiro[4.4]nonane", Russian Journal of Organic Chemistry, vol. 38, No. 4, 2002, pp. 588-590. Translated from Zhurnal Organicheskoi Khimii, vol. 38, No. 4, 2002, pp. 614-616.

Jiang, Jia-Li, et al., "Efficient DMF-Catalyzed Coupling of Epoxides with CO2 under Solvent-Free Conditions to Afford Cyclic Carbonates", Synthetic Communicationsw, 36: 3141-3148, 2006.

Brunner, M., et al., "Kinetic Resolution of Oxiranes by Use of Chiral Lewis Acid Catalysts", Institute of Technical Chemistry and Petrolchernistry. RWTH Aachen, Templergraben 55. 52056 Aachen, FRO.

Tascedda, Patricia, et al., "Electrosynthesis of Benzolactones by Nickel-Catalyzed Carboxylation of Epoxide-Functionalized Aromatic Halides", Synlett 2000, No. 2, 245-247 ISSN 0936-5214.

Qi, Charorong, et al., "Naturally Occurring a-Amino Acid Catalyzed Coupling of Carbon Dioxide with Epoxides to Afford Cyclic Carbonates", SYNLETT 2007, No. 2, pp. 0255-025801.02.207, Advanced online publication: Jan. 24, 2007.

Ochiai, Bungo, et al., "Kinetic and computational studies on aminolysis of bicyclic carbonates bearing alicyclic structure giving alicyclic hydroxyurethanes", Science Direct, Tetrahedron 61 (2005) 1835-1838.

Rodriguez, A., et al., "Total synthesis of lipoxin A4 and lipoxin B4 from butadiene", Tetrahedron Letters 41 (2000) 823-826.

Barbarini, Alessandro, et al., "Cycloaddition of CO2 to epoxides over both homogeneous and silica-supported guanidine catalysts", Tetrahedron Letters 44 (2003) 2931-2934.

Paddock, Robert L., et al., "Co(III) porphyrin/DMAP: an efficient catalyst system for the synthesis of cyclic carbonates from CO2 and epoxides", Science Direct, Tetrahedron Letters 45 (2004) 2023-2026.

Li, Fuwei, et al., "Chemical fixation of CO2 with highly efficient ZnCl2/[BMIm]Br catalyst system", Science Direct, Tetrahedron Letters 45 (2004) 8307-8310.

Du, Ya, et al., "A poly(ethylene glycol)-supported quaternary ammonium salt for highly efficient and environmentally friendly chemical fixation of CO2 with epoxides under supercritical conditions", Science Direct, Tetrahedron Letters 47 (2006) 1271-1275.

Chen, Shu-Wei, et al., "Efficient catalytic synthesis of optically active cyclic carbonates via coupling reaction of epoxides and carbon dioxide", Science Direct, Tetrahedron Letters 48 (2007) 297-300.

Lu, Xiao-Bing, et al., "Catalytic formation of ethylene carbonate from supercritical carbon dioxide/ethylene oxide mixture with tetradentate Schiff-base complexes as catalyst", Applied Catalysis A: General 234 (2002) 25-33.

Lu, Xiao-Bing, et al., "Chemical fixation of CO2 to ethylene carbonate under supercritical conditions: continuous and selective", Applied Catalysis A: General 275 (2004) 73-78.

Paddock, Robert L., et al., "Chiral (salen)CoIII catalyst for the synthesis of cyclic carbonates", Chem. Com mun., 2004, 1622-1623.

Jing, Huanwang, et al., "(Salen)Tin Complexes: Syntheses, Characterization, Crystal Structures, and Catalytic Activity in the Formation of Propylene Carbonate from CO2 and Propylene Oxide", Inorg. Chem. 2004, 43, 4315-4327.

Chen, Peter, et al., "Binding of Propylene Oxide to Porphyrin- and Salen-M(III) Cations, Where M ) Al, Ga, Cr, and Co", Inorg. Chem. 2005, 44, 2588-2595.

Darensbourg, Donald J., et al., "Comparative Kinetic Studies of the Copolymerization of Cyclohexene Oxide and Propylene Oxide with Carbon Dioxide in the Presence of Chromium Salen Derivatives. In Situ FTIR Measurements of Copolymer vs Cyclic Carbonate Production", JACS Articles, Published on Web Jun. 3, 2003, J. Am. Chem. Soc. 2003, 125, 7586-7591.

Lu, Xiao-Bing, et al., "Asymmetric Catalysis with CO2: Direct Synthesis of Optically Active Propylene Carbonate from Racemic Epoxides", JACS Communications, Published on Web Mar. 5, 2004, J. Am. Chem. Soc. 2004, 126, 3732-3733.

Lu, Xiao-Bing, et al., "Highly active electrophile-nucleophile catalyst system for the cycloaddition of CO2 to epoxides at ambient temperature", Science Direct, Journal of Catalysis 227 (2004) 537-541.

Alvaro, Mercedes, et al., "CO2 fixation using recoverable chromium salen catalysts: use of ionic liquids as cosolvent or high-surface-area silicates as supports", Science Direct, Journal of Catalysis 228 (2004) 254-258.

Lu, Xiao-Bing, et al., "Synthesis of ethylene carbonate from supercritical carbon dioxide/ethylene oxide mixture in the presence of bifunctional catalyst", Journal of Molecular Catalysis A: Chemical 186 (2002) 1-11.

Lu, Xiao-Bing, et al., "Chemical fixation of carbon dioxide to cyclic carbonates under extremely mild conditions with highly active bifunctional catalysts", Science Direct, Journal of Molecular Catalysis A: Chemical 210 (2004) 31-34.

Alvaro, Mercedes, et al., "Polymer-bound aluminium salen complex as reusable catalysts for CO2 insertion into epoxides", Science Direct, Tetrahedron 61 (2005) 12131-12139.

Kroger, Mario, et al., "Alternating Copolymerization of Carbon Dioxide and Cyclohexene Oxide and Their Terpolymerization with Lactide Catalyzed by Zinc Complexes of N,N Ligands", Adv. Synth. Catal. 2006, 348, 1908-1918.

Lu, Xiao-Bing, et al., "Highly Active, Binary Catalyst Systems for the Alternating Copolymerization of CO2 and Epoxides under Mild Conditions", Angew. Chem. Int. Ed. 2004, 43, 3574-3577.

Darensbourg, Donald J., et al., "Probing the mechanistic aspects of the chromium salen catalyzed carbon dioxide/epoxide copolymerization process using in situ ATR/FTIR", Science Direct, Catalysis Today 98 (2004) 485-492.

Stamp, Louise M., et al., "Polymer supported chromium porphyrin as catalyst for polycarbonate formation in supercritical carbon dioxide", Chem. Commun., 2001, 2502-2503.

Darensbourg, Donald J., et al., "Solid-State Structures of Zinc(II) Benzoate Complexes. Catalyst Precursors for the Coupling of Carbon Dioxide and Epoxides", Inorg. Chem. 2002, 41, 973-980.

Darensbourg, Donald J., et al., "The Copolymerization of Carbon Dioxide and [2-(3,4-Epoxycyclohexyl)ethyl] trimethoxysilane Catalyzed by (Salen)CrCl. Formation of a CO2 Soluble Polycarbonate", Inorg. Chem. 2003, 42, 4498-4500.

Darensbourg, Donald J., et al., "Cyclohexene Oxide/CO2 Copolymerization Catalyzed by Chromium(III) Salen Complexes and N-Methylimidazole: Effects of Varying Salen Ligand Substituents and Relative Cocatalyst Loading", Inorg. Chem. 2004, 43, 6024-6034.

Darensbourg, Donald J., et al., "Aluminum Salen Complexes and Tetrabutylammonium Salts: A Binary Catalytic System for Production of Polycarbonates from CO2 and Cyclohexene Oxide", Inorg. Chem. 2005, 44, 1433-1442.

Darensbourg, Donald J., et al., "Effective, Selective Coupling of Propylene Oxide and Carbon Dioxide to Poly(Propylene Carbonate) Using (Salen)CrN3 Catalysts", Inorg. Chem. 2005, 44, 4622-4629.

Darensbourg, Donald J., et al., "Syntheses and Structures of Epoxide Adducts of Soluble Cadmium(I1) Carboxylates. Models for the Initiation Process in EpoxideKOz Coupling Reactions", J. Am. Chem. Soc. 1995,117, 538-539.

Cheng, Ming, et al., "Catalytic Reactions Involving C1 Feedstocks: New High-Activity Zn(II)-Based Catalysts for the Alternating Copolymerization of Carbon Dioxide and Epoxides", J. Am. Chem. Soc. 1998, 120, 11018-11019.

(56) References Cited

OTHER PUBLICATIONS

Darensbourg, Donald J., et al., "Bis 2,6-difluorophenoxide Dimeric Complexes of Zinc and Cadmium and Their Phosphine Adducts: Lessons Learned Relative to Carbon Dioxide/Cyclohexene Oxide Alternating Copolymerization Processes Catalyzed by Zinc Phenoxides", J. Am. Chem. Soc. 2000, 122, 12487-12496.

Allen, Scott D., et al., "High-Activity, Single-Site Catalysts for the Alternating Copolymerization of CO2 and Propylene Oxide", JACS Communications, Published on Web Nov. 8, 2002, J. Am. Chem. Soc. 2002, 124, 14284-14285.

Darensbourg, Donald J., et al., "Mechanistic Aspects of the Copolymerization Reaction of Carbon Dioxide and Epoxides, Using a Chiral Salen Chromium Chloride Catalyst", JACS Articles, J. Am. Chem. Soc. 2002, 124, 6335-6342.

Lu, Xiao-Bing, et al., "Design of Highly Active Binary Catalyst Systems for CO2/Epoxide Copolymerization: Polymer Selectivity, Enantioselectivity, and Stereochemistry Control", JACS Articles, J. Am. Chem. Soc. 2006, 128, 1664-1674.

Darensbourg, Donald J., et al., "Supercritical carbon dioxide as solvent for the copolymerization of carbon dioxide and propylene oxide using a heterogeneous zinc carboxylate catalyst", Journal of Molecular Catalysis A: Chemical 104 (1995) LI-L4.

Walther, Martin, et al., "Synthesis of Azolyl Carboximidamides as Ligands for Zn(II) and Cu(II): Application of the Zn(II) Complexes as Catalysts for the Copolymerization of Carbon Dioxide and Epoxides1", JOC Article, J. Org. Chem. 2006, 71, 1399-1406.

Darensbourg, Donald J., et al., "Catalytic Activity of Zinc(I1) Phenoxides Which Possess Readily Accessible Coordination Sites. Copolymerization and Terpolymerization of Epoxides and Carbon Dioxide", American Chemical Society, Macromolecules 1995,28, 7577-7579.

Mang, Stephan, et al., "Copolymerization of CO2 and 1,2-Cyclohexene Oxide Using a CO2-Soluble Chromium Porphyrin Catalyst", American Chemical Society, Macromolecules 2000, 33, 303-308.

Darensbourg, Donald J., et al., "Pressure Dependence of the Carbon Dioxide/Cyclohexene Oxide Coupling Reaction Catalyzed by Chromium Salen Complexes. Optimization of the Comonomer-Alternating Enchainment Pathway", American Chemical Society, Organometallics 2005, 24, 144-148.

Darensbourg, Donald J., et al., "Copolymerization of CO2 and Epoxides Catalyzed by Metal Salen Complexes", Acc. Chem. Res. 2004, 37, 836-844.

Coates, Geoffrey W., et al., "Discrete Metal-Based Catalysts for the Copolymerization of CO2 and Epoxides: Discovery, Reactivity, Optimization, and Mechanism", Angew. Chem. Int. Ed. 2004, 43,6618-6639.

Baiker, Alfons, "Utilization of carbon dioxide in heterogeneous catalytic synthesis", Applied Organometallic Chemistry, Appl. Organometal. Chem. 14, 751-762 (2000).

"The contribution of the utilization option to reducing the CO2 atmospheric loading: research needed to overcome existing barriers for a full exploitation of the potential of the CO2 use", Science Direct, Catalysis Today 98 (2004) 455-462.

Omae, Iwao, "Aspects of carbon dioxide utilization", Science Direct, Catalysis Today 115 (2006) 33-52.

Zevenhoven, Ron, et al., "Chemical fixation of CO2 in carbonates: Routes to valuable products and long-term storage", Science Direct, Catalysis Today 115 (2006) 73-79.

Yoshida, M., et al., Synthesis of Cyclic Carbonates, Recycling of CO2, Chem. Eur. J. 2004, 10, 2886-2893.

Braunstein, Pierre, et al., "Reactions of Carbon Dioxide with Carbon-Carbon Bond Formation Catalyzed by Transition-Metal Complexes", American Chemical Society, Chem. Rev. 1980, 88, 747-764.

Gibson, Dorothy H., "The Organometallic Chemistry of Carbon Dioxide", American Chemical Society, Chem. Rev. 1996, 96, 2063-2095.

Shaikh, Abbas-Alli G., "Organic Carbonates", American Chemical Society, Chem. Rev. 1996, 96, 951-976.

Arakawa, Hironori, et al., "Catalysis Research of Relevance to Carbon Management: Progress, Challenges, and Opportunities", American Chemical Society, Chem. Rev. 2001, 101, 953-996.

Dell'Amico, Daniela Belli, et al., "Converting Carbon Dioxide into Carbamato Derivatives", American Chemical Society, Chem. Rev. 2003, 103, 3857-3897.

Darensbourg, Donald J., et al., "Catalysts for the reactions of epoxides and carbon dioxide", Coordination Chemistry Reviews, 153 (1996) 155-174.

Leitner, W., "The coordination chemistry of carbon dioxide", Coordination Chemistry Reviews, 153 (1996) 257-284.

Ungvary, Ferenc, Application of transition metals in hydroformylation. Annual survey covering the year 1995, Coordination Chemistry Reviews, 160 (1997) 129-159.

Ungvary, Ferenc, Application of transition metals in hydroformylation: annual survey covering the year 1996, Coordination Chemist Reviews, 167 (1997) 233-260.

Ungvary, Ferenc, "Hydroformylation", Coordination Chemist Reviews, 170 (1998) 245-281.

Yin, Xiaolong, et al., "Recent developments in the activation of carbon dioxide by metal complexes", Coordination Chemistry Reviews, 181 (1999) 27-59.

Walther, Dirk, et al., "Carbon dioxide and metal centres: from reactions inspired by nature to reactions in compressed carbon dioxide as solvent", Coordination Chemistry Reviews, 182 (1999) 67-100.

Tanaka, Koji, et al., "Multi-electron reduction of CO2 via Ru—CO2, —C(O)OH, —CO, —CHO, and —H2OH species", Coordination Chemistry Reviews 226 (2002) 211-218.

Ungvary, Ferenc, "Application of transition metals in hydroformylation annual survey covering the year 2001", Coordination Chemistry Reviews 228 (2002) 61-82.

Ungvary, Ferenc, "Application of transition metals in hydroformylation annual survey covering the year 2002", Science Direct, Coordination Chemistry Reviews 241 (2003) 295-312.

Jessop, Philip G., et al., "Recent advances in the homogeneous hydrogenation of carbon dioxide", Science Direct, Coordination Chemistry Reviews 248 (2004) 2425-2442.

Ungvary, Ferenc, "Application of transition metals in hydroformylation annual survey covering the year 2003", Science Direct, Coordination Chemistry Reviews 248 (2004) 867-880.

Xiaoding, Xu, et al., "Mitigation of CO2 by Chemical Conversion: Plausible Chemical Reactions and Promising Products", American Chemical Society, Energy & Fuels 1996, 10, 305-325.

Pacheco, Michael A., et al., "Review of Dimethyl Carbonate (DMC) Manufacture and Its Characteristics as a Fuel Additive", American Chemical Society, Energy & Fuels 1997, 11, 2-29.

"Green Chemical Processing Using CO2", American Chemical Society, Ind. Eng. Chem. Res. 2003, 42, 1598-1602.

Sun, Jianmin, et al., "Development in the green synthesis of cyclic carbonate from carbon dioxide using ionic liquids", Science Direct, Journal of Organometallic Chemistry 690 (2005) 3490-3497.

Sugimoto, Hiroshi, et al., "Copolymerization of Carbon Dioxide and Epoxide", Journal of Polymer Science: Part A: Polymer Chemistry, vol. 42, 5561-5573 (2004).

Carmona, Ernesto, et al., "Electron-rich metal complexes for C02 and CS2 incorporation", Pure & Appl. Chem., vol. 61, No. 10, pp. 1701-1706, 1989.

Aresta, Michele, "Carbon dioxide asa building-block for molecular organic compounds", The Chemical Society, RSC Wokshop, Burlington House, Jul. 27, 2006.

Rayner, Prof. Chris, "Converting carbon dioxide to chemicals", Burlington House, Jul. 27, 2006, RSC Advancing the Chemical Sciences.

Green, Malcolm, "Converting CO2 into Chemicals", RSC Environment, Sustainability and Energy Forum, Oxford University, Jul. 2006.

Lu X-B et al.: "Highly active electrophile-nucleophile catalyst system for the cycloaddition of CO2 to epoxides at ambient temperature" Journal of Catalysts, Academic Press, Duluth, MN, US, vol. 227, No. 2, Oct. 25, 2004, pp. 537-541, XP004583891.

D.A. Atwood, M.J. Harvey: "Group 13 Compounds incorporating Salen Ligands" Chem. Rev., vol. 101, 2001, pp. 37-52, XP002496197.

(56) References Cited

OTHER PUBLICATIONS

Donald J. Darensbourg; Making Plastics from Carbon Dioxide: Salen Metal Complexes as Catalysts for the Production of Polycarbonates from Epoxides and C02: Chemical Review: 2007, vol. 107, No. 6 pp. 2388-2410; D American Chemical Society; Published on Web Apr. 21, 2007.

Donald J. Darensbourg, Paolo Bottarelli, Jeremy R. Andreatta; Inquiry into the Formation of Cyclic Carbonates during the (Salen)CrX Catalyzed C02/Cyciohexene Oxide Copolymerization Process in the Presense of Ionic Initiators; Macromolecules; 2007, vol. 40, No. 21, pp. 7727-7729: American Chemical Society; Published on D Web 9118/2007.

North M .. Young C. Bimetallic aluminium(acen) complexes as catalysts for the synthesis of cyclic carbonates from carbon dioxide and epoxides. Catalysis Science & Technology 2011.1(1).93-99.

Melendez, J., North M, Villuendas P, Young C. One-component bimetallic aluminium(salen)-based catalysts for cyclic carbonate synthesis and their immobilization. Dalton Transactions 2011, 40(15), 3885-3902.

\* cited by examiner

SYNTHESIS OF CYCLIC CARBONATES

CROSS-REFERENCE TO RELATED APPLICATIONS

This application claims priority to International Application No. PCT/GB2008/001485, filed on Apr. 25, 2008, which claims priority to Great Britain Patent Application No. 0708016.1, filed Apr. 25, 2007, each of which is incorporated by reference in its entirety.

The present invention relates to a process for synthesising cyclic carbonates from epoxides and carbon dioxide using aluminium(salen) complexes as catalysts. The invention also provides a method for manufacturing aluminium(salen) complexes and further provides novel aluminium(salen) complexes.

Cyclic carbonates are commercially important products currently manufactured on a multi-tonne scale for use as polar aprotic solvents, additives, antifoam agents for anti-freeze, plasticisers, and monomers for polymer synthesis (see Darensbourg, et al., *Coord. Chem. Rev.,* 153 (1996), 155-174; Coates, et al., *Angew. Chem. Int. Ed.,* 43 (2004), 6618-6639).

The synthesis of cyclic carbonates generally involves the reaction of epoxides with carbon dioxide, and hence could be used to sequestrate carbon dioxide, thus reducing the level of greenhouse gases in the atmosphere.

Catalysts for the synthesis of cyclic carbonates from epoxides and carbon dioxide are known in the art (see Darensbourg, et al., *Coord. Chem. Rev.,* 153 (1996), 155-174; Yoshida, et al., *Chem. Eur. J.,* 10 (2004), 2886-2893; Sun, et al., *J. Organomet. Chem.,* 690 (2005), 3490-3497) although these require elevated reaction temperatures and/or high pressures of carbon dioxide, the reaction often being conducted in supercritical carbon dioxide (see Lu, et al., *App. Cat. A,* 234 (2002), 25-33).

Ratzenhofer, et al., (*Angew. Chemie Int. Ed. Engl.,* 19 (1980), 317-318) succeeded in carrying out the reaction between 2-methyloxirane and carbon dioxide at room temperature and atmospheric pressure using catalysts consisting of a mixture of a metal halide and a Lewis base. However, a long reaction time of 7 days was required. Kisch, et al., (*Chem. Ber.,* 119 (1986), 1090-1094), carrying out the same reaction under the same conditions and also using catalysts of this type, reports a reaction time of 3.5 to 93 hours using up to 4 mol % of a $ZnCl_2$ catalyst and up to 16 mol % of a $(nButyl)_4$NI catalyst.

Lu, et al., (*J. Mol. Cat. A,* 210 (2004), 31-34; *J. Cat.,* 227 (2004), 537-541) describe the use of tetradentate Schiff-base aluminium complexes in conjunction with a quaternary ammonium salt or polyether-KY complexes as catalyst systems for the reaction of various epoxides with carbon dioxide at room temperature and about 6 atmospheres.

Metal(salen) complexes, including aluminium(salen) complexes, are well-known in the art for their use as catalysts. Lu, et al., *App. Cat. A,* 234 (2002), 25-33, describes the use of a monomeric aluminium(salen) catalyst.

Also known in the art is the method of synthesising aluminium(salen) catalysts by treating a salen ligand with $Me_3Al$, $Et_3Al$, $Me_2AlCl$, $Me_2AlOTf$, $Et_2AlBr$ or $Et_2AlCl$ in a two-stage process (reviewed in Atwood and Harvey, *Chem. Rev.,* 2001, 101, 37-52).

It has been found by the inventor that dimeric aluminium (salen) complexes are highly active catalysts for the reaction of epoxides with carbon dioxide to produce cyclic carbonates, and allow the reaction to be carried out at room temperature and atmospheric pressure, using short reaction times and commercially viable amounts of catalyst.

Accordingly a first aspect of the invention provides a process for the production of cyclic carbonates comprising contacting an epoxide with carbon dioxide in the presence of a dimeric aluminium(salen) catalyst and a co-catalyst capable of supplying $Y^-$, where Y is selected from Cl, Br and I. The dimeric aluminium(salen) catalysts are of formula I:

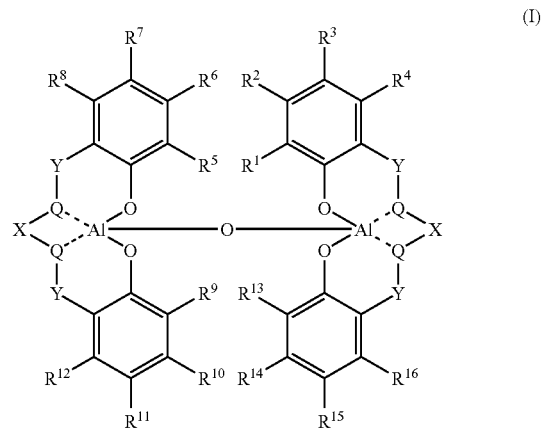

(I)

wherein:

Y-Q is $CR^{C1}$=N or $CR^{C1}R^{C2}$—$NR^{N1}$, where $R^{C1}$, $R^{C2}$ and $R^{N1}$ are independently selected from H, halo, optionally substituted $C_{1-20}$ alkyl, optionally substituted $C_{5-20}$ aryl, ether and nitro;

each of the substituents $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$, is independently selected from H, halo, optionally substituted $C_{1-20}$ alkyl (including $CAr_3$, where Ar is a $C_{5-20}$ aryl group), optionally substituted $C_{5-20}$ aryl, optionally substituted $C_{3-20}$ heterocyclyl, ether, ammonium and nitro;

X is either of the formula —$(CH_2)_n$— or —O—$(CH_2)_p$—O—, where n is 2, 3, 4, or 5 and p is 1, 2, or 3, or represents a divalent group selected from $C_{5-7}$ arylene, $C_{5-7}$ cyclic alkylene and $C_{3-7}$ heterocyclylene, which may be optionally substituted.

If the catalyst of formula I includes one or more chiral centres, then it may be a (wholly or partially) racemic mixture or other mixture thereof, for example, a mixture enriched in one enantiomer or diastereoisomer, a single enantiomer or diastereoisomer, or a mixture of the stereoisomers. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner. Preferably the catalyst of formula I is a single enantiomer, if a chiral centre is present.

The cocatalyst is preferably soluble in the reaction mixture. Suitable sources of $Y^-$ are MY, where M is a suitable cation, such as onium halides, which include, but are not limited to, $R_4NY$, $R_3SY$, $R_4PY$ and $R_4SbY$, where each R is independently selected from optionally substituted $C_{1-10}$ alkyl, $C_{3-20}$ heterocyclyl and $C_{5-20}$ aryl groups and one R can be an acyl group, and simple halides, e.g. NaCl, KI.

The reaction of the first aspect may be defined as follows:

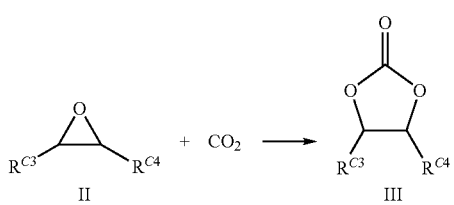

wherein $R^{C3}$ and $R^{C4}$ are independently selected from H, optionally substituted $C_{1-10}$ alkyl, optionally substituted $C_{3-20}$ heterocyclyl and optionally substituted $C_{5-20}$ aryl, or $R^{C3}$ and $R^{C4}$ form an optionally substituted linking group between the two carbon atoms to which they are respectively attached. The linking group, together with the carbon atoms to which it is attached, may form an optionally substituted $C_{5-20}$ cycloalkyl or $C_{5-20}$ heterocylyl group. The $C_{5-20}$ cycloalkyl or $C_{5-20}$ heterocylyl group may be substituted only in a single position on the ring, for example, adjacent the epoxide. Suitable substituents, include optionally substituted $C_{1-10}$ alkyl, optionally substituted $C_{3-20}$ heterocyclyl and optionally substituted $C_{5-20}$ aryl.

A possible substituent for the $C_{1-10}$ alkyl group is a $C_{5-20}$ aryl group. A further possible group of substituents includes, but is not limited to, a $C_{5-20}$ aryl group (e.g. phenyl, 4-methoxy phenyl), a hydroxy group, a halo group (e.g. Cl), a acetyl group, an ester group, or a $C_{5-20}$ aryloxy group (e.g. phenoxy).

The first aspect of the invention also provides the use of a dimeric aluminium(salen) catalyst of formula I and a co-catalyst capable of supplying $Y^-$ as a catalyst system for the production of cyclic carbonates from epoxides.

The dimeric aluminium(salen) catalysts of the first aspect may be of formula Ia:

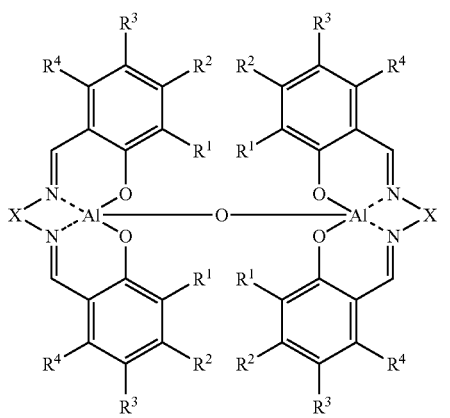

where $R^1$, $R^2$, $R^3$, $R^4$ and X are as defined above.

A second aspect of the invention provides a process for the synthesis of a dimeric aluminium(salen) catalyst of formula Ia comprising treating a salen ligand of formula IV:

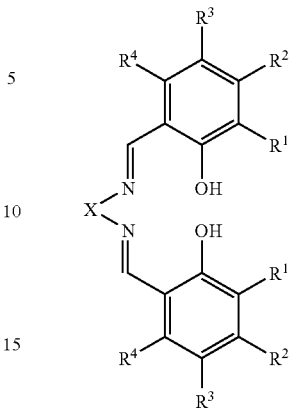

where $R^1$, $R^2$, $R^3$, $R^4$ and X are as defined above, with) $Al(OR^O)_3$ in an organic solvent, wherein $R^O$ is selected from $C_{1-4}$ alkyl and $C_{5-7}$ aryl.

A third aspect of the invention provides novel compounds of formula I.

The catalysts of the present invention may be immobilized on a solid support.

DETAILED DESCRIPTION OF THE INVENTION

Definitions

Epoxide: The term "epoxide", as used herein, may pertain to a compound of the formula

wherein $R^{C3}$ and $R^{C4}$ are independently selected from H, optionally substituted $C_{1-10}$ alkyl, optionally substituted $C_{3-20}$ heterocyclyl and optionally substituted $C_{5-20}$ aryl, or $R^{C3}$ and $R^{C4}$ form an optionally substituted linking group between the two carbon atoms to which they are respectively attached. The linking group, together with the carbon atoms to which it is attached, may form an optionally substituted $C_{5-20}$ cycloalkyl or $C_{5-20}$ heterocylyl group. The $C_{5-20}$ cycloalkyl or $C_{5-20}$ heterocylyl group may be substituted only in a single position on the ring, for example, adjacent the epoxide. Suitable substituents, include optionally substituted $C_{1-10}$ alkyl, optionally substituted $C_{3-20}$ heterocyclyl and optionally substituted $C_{5-20}$ aryl.

The optional substituents may be selected from: $C_{1-10}$ alkyl, $C_{3-20}$ heterocyclyl, $C_{5-20}$ aryl, halo, hydroxy, ether, cyano, nitro, carboxy, ester, amido, amino, acylamido, ureido, acyloxy, thiol, thioether, sulfoxide, sulfonyl, thioamido and sulfonamino.

In some embodiments, the $C_{1-10}$ alkyl group is substituted by a $C_{5-20}$ aryl group. In other embodiments, the $C_{1-10}$ alkyl group may be substituted by a $C_{5-20}$ aryl group (e.g. phenyl, 4-methoxy phenyl), a hydroxy group, a halo group (e.g. Cl), an acetyl group, an ester group, or a $C_{5-20}$ aryloxy group (e.g. phenoxy).

Preferably, the epoxide is a terminal epoxide, i.e. $R^{C4}$=H.

In some embodiments, $R^{C3}$ is selected from optionally substituted $C_{1-4}$ alkyl and optionally substituted $C_{5-7}$ aryl. In some of these embodiments $R^{C3}$ is unsubstituted.

Preferred epoxides are ethylene oxide ($R^{C3}=R^{C4}=H$), propylene oxide ($R^{C3}=$methyl, $R^{C4}=H$), butylene oxide ($R^{C3}=$ethyl, $R^{C4}=H$), and styrene oxide ($R^{C3}=$phenyl, $R^{C4}=H$). Other epoxides of interest include hydroxypropyl oxide ($R^{C3}=CH_2OH$, $R^{C4}=H$), chloropropyl oxide ($R^{C3}=CH_2Cl$, $R^{C4}=H$), acetyloxypropyl oxide ($R^{C3}=CH_2OAc$, $R^{C4}=H$), phenylcarbonyloxypropyl oxide ($R^{C3}=CH_2OCOPh$, $R^{C4}=H$), phenoxypropyl oxide ($R^{C3}=CH_2OPh$, $R^{C4}=H$) and 4-methoxyphenylethyl oxide ($R^{C3}=4\text{-}MeOC_6H_4$, $R^{C4}=H$).

Cyclic carbonate: the term "cyclic carbonate", as used herein, may pertain to a compound of the formula:

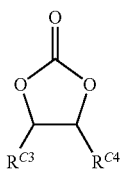

wherein $R^{C3}$ and $R^{C4}$ are as defined above.

Alkyl: The term "alkyl", as used herein, pertains to a monovalent moiety obtained by removing a hydrogen atom from a carbon atom of a hydrocarbon having from 1 to 20 carbon atoms (unless otherwise specified), which may be aliphatic or alicyclic and which may be saturated or unsaturated (e.g. partially saturated, fully unsaturated). Thus, the term "alkyl" includes the sub-classes alkenyl, alkynyl, cycloalkyl, cycloalkenyl, cycloalkynyl, etc., as discussed below.

In the context of alkyl groups, the prefixes (e.g. $C_{1-4}$, $C_{1-7}$, $C_{1-20}$, $C_{2-7}$, $C_{3-7}$, etc.) denote the number of carbon atoms, or the range of number of carbon atoms. For example, the term "$C_{1-4}$ alkyl", as used herein, pertains to an alkyl group having from 1 to 4 carbon atoms. Examples of groups of alkyl groups include $C_{1-4}$ alkyl ("lower alkyl"), $C_{1-7}$ alkyl and $C_{1-20}$ alkyl. Note that the first prefix may vary according to other limitations; for example, for unsaturated alkyl groups, the first prefix must be at least 2; for cyclic alkyl groups, the first prefix must be at least 3; etc.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), and heptyl ($C_7$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl", as used herein, pertains to an alkyl group having one or more carbon-carbon double bonds. Examples of groups of alkenyl groups include $C_{2-4}$ alkenyl, $C_{2-7}$ alkenyl, $C_{2-20}$ alkenyl.

Examples of (unsubstituted) unsaturated alkenyl groups include, but are not limited to, ethenyl (vinyl, $-CH=CH_2$), 1-propenyl ($-CH=CH-CH_3$), 2-propenyl (allyl, $-CH_2-CH=CH_2$), isopropenyl (1-methylvinyl, $-C(CH_3)=CH_2$), butenyl ($C_4$), pentenyl ($C_5$), and hexenyl ($C_6$).

Alkynyl: The term "alkynyl", as used herein, pertains to an alkyl group having one or more carbon-carbon triple bonds. Examples of groups of alkynyl groups include $C_{2-4}$ alkynyl, $C_{2-7}$ alkynyl, $C_{2-20}$ alkynyl.

Examples of (unsubstituted) unsaturated alkynyl groups include, but are not limited to, ethynyl (ethinyl, $-C\equiv CH$) and 2-propynyl (propargyl, $-CH_2-C\equiv CH$).

Cycloalkyl: the term "cycloalkyl", as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g. partially unsaturated, fully unsaturated), which moiety has from 3-20 carbon atoms (unless otherwise specified), including from 3 to 20 ring atoms. Thus, the term "cycloalkyl" includes the sub-classes cycloalkenyl and cycloalkynyl. Preferably, each ring has from 3 to 7 ring atoms. Examples of groups of cycloalkyl groups include $C_{3-20}$ cycloalkyl, $C_{3-15}$ cycloalkyl, $C_{3-10}$ cycloalkyl, $C_{3-7}$ cycloalkyl.

Cyclic alkylene: The teen "cyclic alkylene" as used herein pertains to a divalent moiety obtained by removing a hydrogen atom from each of two adjacent alicyclic ring atoms of a carbocyclic ring of a carbocyclic compound, which carbocyclic ring may be saturated or unsaturated (e.g. partially saturated, fully unsaturated), which moiety has from 3 to 20 carbon atoms (unless otherwise specified), including from 3 to 20 ring atoms. Preferably each ring has from 5 to 7 ring atoms. Examples of groups of cyclic alkylene groups include $C_{3-20}$ cyclic alkylenes, $C_{3-15}$ cyclic alkylenes, $C_{3-10}$ cyclic alkylenes, $C_{3-7}$ cyclic alkylenes.

Examples of cycloalkyl groups and cyclic alkylene groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$;

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$);

saturated polycyclic hydrocarbon compounds:
thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$);

unsaturated polycyclic hydrocarbon compounds:
camphene ($C_{10}$), limonene ($C_{10}$), pinene ($C_{10}$);

polycyclic hydrocarbon compounds having an aromatic ring:
indene ($C_9$), indane (e.g., 2,3-dihydro-1H-indene) ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$).

Heterocyclyl: The term "heterocyclyl", as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

Heterocyclylene: The term "heterocyclylene", as used herein, pertains to a divalent moiety obtained by removing a hydrogen atom from each of two adjacent ring atoms of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

The heterocyclyl or heterocyclylene group may be bonded via carbon or hetero ring atoms. Preferably, the heterocyclylene group is bonded via two carbon atoms.

When referring to heterocyclyl or heterocyclylene groups, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$ heterocyclyl", as used herein, pertains to a heterocyclyl group having 5 or 6 ring atoms. Examples of groups of heterocyclyl groups include $C_{3-20}$ heterocyclyl, $C_{5-20}$ heterocyclyl, $C_{3-15}$ heterocyclyl, $C_{5-15}$ heterocyclyl, $C_{3-12}$ heterocyclyl, $C_{5-12}$ heterocyclyl, $C_{3-10}$ heterocyclyl, $C_{5-10}$ heterocyclyl, $C_{3-7}$ heterocyclyl, $C_{5-7}$ heterocyclyl, and $C_{5-6}$ heterocyclyl.

Similarly, the term "$C_{5-6}$ heterocyclylene", as used herein, pertains to a heterocyclylene group having 5 or 6 ring atoms. Examples of groups of heterocyclylene groups include $C_{3-20}$ heterocyclylene, $C_{5-20}$ heterocyclylene, $C_{3-15}$ heterocyclylene, $C_{5-15}$ heterocyclylene, $C_{3-12}$ heterocyclylene, $C_{5-12}$ heterocyclylene, $C_{3-10}$ heterocyclylene, $C_{5-10}$ heterocyclylene, $C_{3-7}$ heterocyclylene, $C_{5-7}$ heterocyclylene, and $C_{5-6}$ heterocyclylene.

Examples of monocyclic heterocyclyl and heterocyclylene groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl and heterocyclylene groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 carbon atoms.

The ring atoms may be all carbon atoms, as in "carboaryl groups" in which case the group may conveniently be referred to as a "$C_{5-20}$ carboaryl" group.

$C_{5-20}$ arylene: The term "$C_{5-20}$ arylene", as used herein, pertains to a divalent moiety obtained by removing a hydrogen atom from each of two adjacent ring atoms of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 carbon atoms.

The ring atoms may be all carbon atoms, as in "carboarylene groups" in which case the group may conveniently be referred to as a "$C_{5-20}$ carboarylene" group.

Examples of $C_{5-20}$ aryl and $C_{5-20}$ arylene groups which do not have ring heteroatoms (i.e. $C_{5-20}$ carboaryl and $C_{5-20}$ carboarylene groups) include, but are not limited to, those derived from benzene (i.e. phenyl) ($C_6$), naphthalene ($C_{10}$), anthracene ($C_{14}$), phenanthrene ($C_{14}$), and pyrene ($C_{16}$).

Alternatively, the ring atoms may include one or more heteroatoms, including but not limited to oxygen, nitrogen, and sulfur, as in "heteroaryl groups" or "heteroarylene groups". In this case, the group may conveniently be referred to as a "$C_{5-20}$ heteroaryl" or "$C_{5-20}$ heteroarylene" group, wherein "$C_{5-20}$" denotes ring atoms, whether carbon atoms or heteroatoms. Preferably, each ring has from 5 to 7 ring atoms, of which from 0 to 4 are ring heteroatoms.

The heteroaryl or heteroarylene group may be bonded via carbon or hetero ring atoms. Preferably, the heteroarylene group is bonded via two carbon atoms.

Examples of $C_{5-20}$ heteroaryl and $C_{5-20}$ heteroarylene groups include, but are not limited to, $C_5$ heteroaryl and $C_5$ heteroarylene groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, tetrazole and oxatriazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine) and triazine.

Examples of $C_{5-20}$ heteroaryl and $C_{5-20}$ heteroarylene groups which comprise fused rings, include, but are not limited to, $C_9$ heteroaryl and $C_9$ heteroarylene groups derived from benzofuran, isobenzofuran, benzothiophene, indole, isoindole; $C_{10}$ heteroaryl and $C_{10}$ heteroarylene groups derived from quinoline, isoquinoline, benzodiazine, pyridopyridine; $C_{14}$ heteroaryl and $C_{14}$ heteroarylene groups derived from acridine and xanthene.

The above alkyl, cyclic alkylene, heterocyclyl, heterocyclylene, aryl, and arylene groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Nitro: —NO$_2$.

Cyano (nitrile, carbonitrile): —CN.

Acyl (keto): —C(=O)R, wherein R is an acyl substituent, for example, H, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (pivaloyl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinylcarbonyl.

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Examples of amino groups include, but are not limited to, —NH$_2$, —NHCH$_3$, —NHCH(CH$_3$)$_2$, —N(CH$_3$)$_2$, —N(CH$_2$CH$_3$)$_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino. In particular, the cyclic amino groups may be substituted on their ring by any of the substituents defined here, for example carboxy, carboxylate and amido.

Ammonium: —NH$_4^+$Z$^-$, wherein Z$^-$ is an appropriate counterion, such as halide (e.g. Cl$^-$, Br$^-$), nitrate, perchlorate.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably H or a $C_{1-7}$ alkyl group, most preferably H, and R$^2$ is an acyl substituent, for example, a $C_{1-7}$ alkyl group, a $C_{3-20}$ heterocyclyl group, or a $C_{5-20}$ aryl group, preferably a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

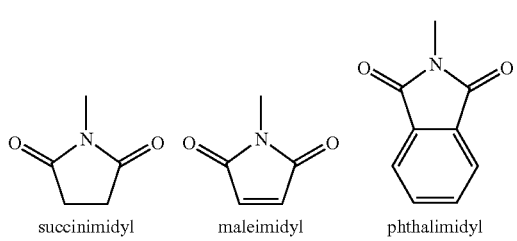

succinimidyl   maleimidyl   phthalimidyl

Ureido: —N(R$^1$)CONR$^2$R$^3$ wherein R$^2$ and R$^3$ are independently amino substituents, as defined for amino groups, and R$^1$ is a ureido substituent, for example, hydrogen, a $C_{1-7}$alkyl group, a $C_{3-20}$heterocyclyl group, or a $C_{5-20}$aryl group, preferably hydrogen or a $C_{1-7}$ alkyl group. Examples of ureido groups include, but are not limited to, —NHCONH$_2$, —NHCONHMe, —NHCONHEt, —NHCONMe$_2$, —NH-CONEt$_2$, —NMeCONH$_2$, —NMeCONHMe, —NMeCONHEt, —NMeCONMe$_2$, —NMeCONEt$_2$ and —NHCONHPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, —OC(=O)C$_6$H$_4$F, and —OC(=O)CH$_2$Ph.

Thiol: —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Sulfoxide (sulfinyl): —S(=O)R, wherein R is a sulfoxide substituent, for example, a $C_{1-7}$ alkyl group, a $C_{3-20}$ heterocyclyl group, or a $C_{5-20}$ aryl group, preferably a $C_{1-7}$ alkyl group. Examples of sulfoxide groups include, but are not limited to, —S(=O)CH$_3$ and —S(=O)CH$_2$CH$_3$.

Sulfonyl (sulfone): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl).

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Sulfonamino: —NR$^1$S(=O)$_2$R, wherein R$^1$ is an amino substituent, as defined for amino groups, and R is a sulfonamino substituent, for example, a $C_{1-7}$alkyl group, a $C_{3-20}$heterocyclyl group, or a $C_{5-20}$aryl group, preferably a $C_{1-7}$alkyl group. Examples of sulfonamino groups include, but are not limited to, —NHS(=O)$_2$CH$_3$, —NHS(=O)$_2$Ph and —N(CH$_3$)S(=O)$_2$C$_6$H$_5$.

As mentioned above, the groups that form the above listed substituent groups, e.g. $C_{1-7}$ alkyl, $C_{3-20}$ heterocyclyl and $C_{5-20}$ aryl, may themselves be substituted. Thus, the above definitions cover substituent groups which are substituted.

Chemically Protected Forms

It may be convenient or desirable to prepare, purify, handle and/or use the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

Unless otherwise specified, a reference to a particular compound also includes chemically protected forms thereof.

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH—Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O●).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

In particular application in the present invention is the protection of hydroxy and amino groups.

Solid Support

Catalysts of the present invention may be immobilized on a solid support by:
(a) steric trapping; or
(b) electrostatic binding.

These methods are reviewed by Carlos Baleizão and Hermenegildo Garcia in "Chiral Salen Complexes An Overview to Recoverable and Reusable Homogeneous and Heterogeneous Catalysts" (*Chem. Rev.* 2006, 106, 3987-4043).

For steric trapping, the most suitable class of solid support is zeolites, which may be natural or modified. The pore size must be sufficiently small to trap the catalyst but sufficiently large to allow the passage of reactants and products to and from the catalyst. Suitable zeolites include zeolites X, Y and EMT as well as those which have been partially degraded to provide mesopores, that allow easier transport of reactants and products.

For the electrostatic binding of the catalyst to a solid support, typical solid supports may include silica, Indian clay, Al-pillared clay, Al-MCM-41, K10, laponite, bentonite, and zinc-alumium layered double hydroxide. Of these silica and montmorillonite clay are of particular interest.

Catalysed Reactions

In one aspect of the present invention, there is provided a process for the production of cyclic carbonates comprising contacting an epoxide with carbon dioxide in the presence of a dimeric aluminium(salen) catalyst of formula I, preferably of formula Ia, and a co-catalyst which is a source of Y$^-$.

This reaction has the advantage that it may be carried out at easily accessible temperatures of between 0 and 40° C. and pressures of between 0.5 and 2 atm. Preferably, the reaction temperature lies between 20 and 30° C. Yields of over 50% may be achieved with short reaction times of 3 to 24 hours, using commercially viable amounts of catalyst, that is, from 0.1 to 10 mol %, preferably 0.1 to 2.5 mol %. In some cases, yields of over 70% or over 90% may be achieved under these conditions.

Preferably, the aluminium(salen) catalyst of formula I is symmetrical, such that $R^1=R^{13}$, $R^2=R^{14}$, $R^3=R^{15}$, $R^4=R^{16}$, $R^5=R^9$, $R^6=R^{10}$, $R^7=R^{11}$, and $R^8=R^{12}$. More preferably $R^1$, $R^5$, $R^9$, and $R^{13}$ are identical, $R^2$, $R^6$, $R^{10}$ and $R^{14}$ are identical, $R^3$, $R^7$, $R^{11}$, and $R^{15}$ are identical, and $R^4$, $R^8$, $R^{12}$ and $R^{16}$ are identical. Such catalysts are of formula Ia, which may be preferred.

In some embodiments, X is —(CH$_2$)$_n$— or —O—(CH$_2$)$_p$—O—, where n is 2, 3, 4, or 5 and p is 1, 2, or 3. In these embodiments, n is preferably 2 or 3 and p is preferably 1 or 2. n is more preferably 2. In some embodiments, n is preferably 3. In these embodiments X is preferably —(CH$_2$)$_n$— (e.g. —C$_2$H$_4$—, —C$_3$H$_6$—).

In other embodiments, X represents a divalent group selected from C$_{5-7}$ arylene, C$_{5-7}$ cyclic alkylene and C$_{3-7}$ heterocyclylene, which may be optionally substituted. Preferably X represents C$_{5-7}$ cyclic alkylene, and more preferably C$_6$ cyclic alkylene. This group is preferably saturated, and therefore is the group:

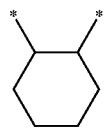

In other preferred embodiments, X represents C$_{5-7}$ arylene, which is more preferably C$_6$ arylene, and in particular, benzylene:

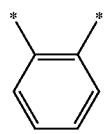

When X represents a divalent group selected from C$_{5-7}$ arylene, C$_{5-7}$ cyclic alkylene and C$_{3-7}$ heterocyclylene, it may preferably be unsubstituted. If it is substituted, then the substituents may be selected from nitro, halo, C$_{1-4}$ alkyl, including substituted C$_{1-4}$ alkyl, (e.g. methyl, benzyl), C$_{1-4}$ alkoxy (e.g. methoxy) and hydroxy.

Preferably Y-Q is $CR^{C1}=N$, wherein $R^{C1}$ is as defined above. $R^{C1}$ is preferably selected from H and $C_{1-4}$ alkyl. More preferably Y-Q is CH=N.

If Y-Q is $CR^{C1}R^{C2}-NR^{N1}$, then in some embodiments $R^{C1}$, $R^{C2}$ and $R^{N1}$ are H.

Preferably $R^4=R^8=R^{12}=R^{16}=H$. Preferably $R^1$, $R^2$, $R^3$, $R^5$, $R^6$, $R^7$, $R^9$, $R^{10}$, $R^{11}$, $R^{13}$, $R^{14}$, and $R^{15}$ are independently selected from H, $C_{1-7}$ alkyl, ether and nitro.

If a group selected from $R^1$, $R^2$, $R^3$, $R^5$, $R^6$, $R^7$, $R^9$, $R^{10}$, $R^{11}$, $R^{13}$, $R^{14}$, and $R^{15}$ is ether, then the ether group is preferably a $C_{1-7}$ alkoxy group and more preferably $C_{1-4}$ alkoxy group, e.g. methoxy.

If a group selected from $R^1$, $R^2$, $R^3$, $R^5$, $R^6$, $R^7$, $R^9$, $R^{10}$, $R^{11}$, $R^{13}$, $R^{14}$, and $R^{15}$ is $C_{1-7}$ alkyl, it is preferably butyl, more preferably tert-butyl. In other embodiments, the $C_{1-7}$ alkyl is preferably optionally substituted methyl, e.g. $diC_{1-4}$ alkylamino substituted methyl (diethylaminomethyl).

A particularly preferred set of embodiments of the catalyst of formula Ia have:
Y-Q is CH=N;
X as:
(i) —$C_2H_4$—;
(ii) 1,2 $C_6$ cyclic alkylene; or
(iii) 1,2 benzylene;
$R^4$=H;
$R^1$, $R^2$ and $R^3$ selected from H, tert-butyl, methoxy and nitro, where only one of these three groups can be nitro.

A further particularly preferred set of embodiments of the catalyst of formula Ia have:
Y-Q is CH=N;
X as:
(iii) 1,2 benzylene;
(iv) —$C_3H_6$—
$R^4$=H;
one of $R^1$, $R^2$ and $R^3$ is $diC_{1-4}$ alkyl amino methyl, and the others of $R^1$, $R^2$ and $R^3$ are H.

The cocatalyst is a source of $Y^-$, and in particular MY, where M is a suitable cation, such as onium halides, which include, but are not limited to, $R_4$NY, $R_3$SY, $R_4$PY and $R_4$SbY, where each R is independently selected from optionally substituted $C_{1-10}$ alkyl, $C_{3-20}$ heterocyclyl and $C_{5-20}$ aryl groups and one R can be an acyl group, and simple halides, e.g. NaCl, KI.

It is preferred that the co-catalyst for this reaction is of the form $R_4$NY, where each R is independently $C_{1-10}$ alkyl and Y is selected from I, Br and Cl. R is preferably selected from $C_{3-5}$ alkyl, and more preferably is butyl. Y is preferably Br. Therefore, a particularly preferred co-catalyst is $Bu_4$NBr. The amount of co-catalyst is preferably 0.1 to 10 mol %, more preferably 0.1 to 2.5 mol %.

The reaction may be carried out under solvent-free conditions, depending on the epoxides used. In some cases, the epoxides may act as a solvent for the catalyst.

Manufacture of Dimeric Aluminium(Salen) Complexes

In a second aspect of the invention, there is provided a process for the production of dimeric aluminium(salen) catalysts of formula Ia comprising treating a salen ligand of formula IV with $Al(OR^O)_3$ in an organic solvent, wherein $R^O=C_{1-4}$ alkyl or $C_{5-7}$ aryl.

The organic solvent can be an aprotic solvent. Preferably, the organic solvent is toluene. It is also preferred that $R^O$ is $C_{1-4}$ alkyl and more preferably ethyl. The reaction time preferably lies between 2 and 18 hours, more preferably between 3 and 10 hours.

The reaction may be heated, if required, by any conventional means. In some embodiments, the carbon dioxide may be supplied heated, and in other embodiments, the reaction may be heated by a convention or microwave system.

Novel Dimeric Aluminium(Salen) Complexes

In a third aspect of the invention there are provided novel aluminium(salen) complexes of formula I. In particular, these novel catalysts may have:
at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, or $R^{16}$ as nitro;
at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, or $R^{16}$ as ether.

In general, the preferences expressed in regard the first aspect of the invention may apply to the third aspect, provided that they are compatible with the above statements.

Preferably, the aluminium(salen) catalyst of formula I is symmetrical, such that $R^1=R^{13}$, $R^2=R^{14}$, $R^3=R^{15}$, $R^4=R^{16}$, $R^5=R^9$, $R^6=R^{10}$, $R^7=R^{11}$, and $R^8=R^{12}$. More preferably $R^1$, $R^5$, $R^9$, and $R^{13}$ are identical, $R^2$, $R^6$, $R^{10}$ and $R^{14}$ are identical, $R^3$, $R^7$, $R^{11}$, and $R^{15}$ are identical, and $R^4$, $R^8$, $R^{12}$ and $R^{16}$ are identical. Such catalysts are of formula Ia.

In some embodiments, X is —$(CH_2)_n$— or —O—$(CH_2)_p$—O—, where n is 2, 3, 4, or 5 and p is 1, 2, or 3. In these embodiments, n is preferably 2 or 3 and p is preferably 1 or 2. n is more preferably 2. In these embodiments X is preferably —$(CH_2)_n$— (e.g. —$C_2H_4$—).

In other embodiments, X represents a divalent group selected from $C_{5-7}$ arylene, $C_{5-7}$ cyclic alkylene and $C_{3-7}$ heterocyclylene, which may be optionally substituted. Preferably X represents $C_{5-7}$ cyclic alkylene, and more preferably $C_6$ cyclic alkylene. This group is preferably saturated, and therefore is the group:

In other preferred embodiments, X represents $C_{5-7}$ arylene, which is more preferably $C_6$ arylene, and in particular, benzylene:

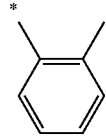

When X represents a divalent group selected from $C_{5-7}$ arylene, $C_{5-7}$ cyclic alkylene and $C_{3-7}$ heterocyclylene, it may preferably be unsubstituted. If it is substituted, then the substituents may be selected from $C_{1-4}$ alkyl (e.g. methyl), $C_{1-4}$ alkoxy (e.g. methoxy) and hydroxy.

Preferably Y-Q is $CR^{C1}=N$, wherein $R^{C1}$ is as defined above. $R^{C1}$ is preferably selected from H and $C_{1-4}$ alkyl. More preferably Y-Q is CH=N.

If Y-Q is $CR^{C1}R^{C2}-NR^{N1}$ then in some embodiments $R^{C1}$, $R^{C2}$ and $R^{N1}$ are H.

Preferably $R^4=R^8=R^{12}=R^{16}=H$. Preferably $R^1$, $R^2$, $R^3$, $R^5$, $R^6$, $R^7$, $R^9$, $R^{10}$, $R^{11}$, $R^{13}$, $R^{14}$, and $R^{15}$ are independently selected from H, $C_{1-7}$ alkyl, ether and nitro.

If a group selected from $R^1$, $R^2$, $R^3$, $R^5$, $R^6$, $R^7$, $R^9$, $R^{10}$, $R^{11}$, $R^{13}$, $R^{14}$, and $R^{15}$ is ether, then the ether group is preferably a $C_{1-7}$ alkoxy group and more preferably $C_{1-4}$ alkoxy group, e.g. methoxy.

If a group selected from $R^1$, $R^2$, $R^3$, $R^5$, $R^6$, $R^7$, $R^9$, $R^{10}$, $R^{11}$, $R^{13}$, $R^{14}$, and $R^{15}$ is $C_{1-7}$ alkyl, it is preferably butyl, more preferably tert-butyl.

More preferably, the catalyst is of formula Ia.

A particularly preferred set of embodiments of the novel catalyst of formula Ia have:
Y-Q is CH=N;
X as 1,2 $C_6$ cyclic alkylene;
$R^4$=H; and
 (i) $R^1$=$R^3$=tert-butyl and $R^2$=H;
 (ii) $R^1$=$R^3$=H and $R^2$=methoxy;
 (iii) $R^1$=$R^2$=$R^3$=H;
 (iv) $R^1$=tert-butyl and $R^2$=$R^3$=H; or
 (v) $R^1$=tert-butyl, $R^2$=H and $R^3$=methoxy.

A further particularly preferred set of embodiments of the catalyst of formula Ia have:
Y-Q is CH=N;
X as:
 (iii) 1,2 benzylene;
 (iv) —$C_3H_6$—
$R^4$=H;
one of $R^1$, $R^2$ and $R^3$ is $diC_{1-4}$ alkyl amino methyl, and the others of $R^1$, $R^2$ and $R^3$ are H.

EXAMPLES

General Experimental Methods

IR spectroscopy
IR spectra of liquids or of solids dissolved in a solvent were recorded between NaCl plates on a PE Spectrum 1 spectrometer. IR spectra of pure solids were recorded on a Nicolet380 FTIR spectrometer fitted with a 'Smart orbit' attachment.
NMR
All NMR spectra were recorded at ambient temperature on a Bruker Avance 300 spectrometer. The sample was dissolved in $CDCl_3$ unless specified otherwise.
Mass Spectroscopy
low resolution EI and CI spectra were recorded on a Varian Saturn 2200 GC-mass spectrometer. Low and high resolution electrospray spectra were recorded on a Waters LCT Premier mass spectrometer.

Example 1

General Procedure for the Synthesis of Catalysts 1a-h

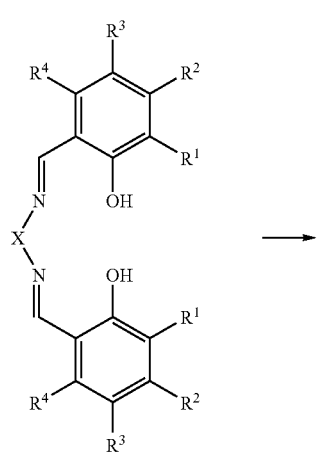

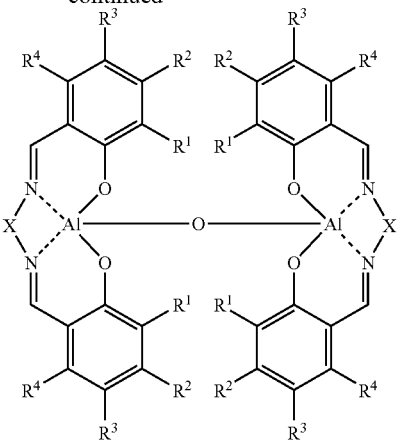

1a: X=(1R,2R)-cyclohexyl; $R^1$=$R^3$=$^tBu$; $R^2$=$R^4$=H
1b: X=(1R,2R)-cyclohexyl; $R^1$=$^tBu$; $R^2$=$R^4$=H; $R^3$=$NO_2$
1c: X=$(CH_2)_2$; $R^1$=$R^3$=$^tBu$; $R^2$=$R^4$=H
1d: X=1,2-$C_6H_4$; $R^1$=$R^3$=$^tBu$; $R^2$=$R^4$=H
1e: X=(1R,2R)-cyclohexyl; $R^1$=$R^3$=$R^4$=H; $R^2$=OMe
1f: X=(1R,2R)-cyclohexyl; $R^1$=$R^2$=$R^3$=$R^4$=H
1g: X=(1R,2R)-cyclohexyl; $R^1$=$^tBu$; $R^2$=$R^3$=$R^4$=H;
1h: X=(1R,2R)-cyclohexyl; $R^1$=$^tBu$; $R^2$=H; $R^3$=OMe; $R^4$=H $Al(OEt)_3$ (0.28 g, 1.72 mmol) was added to dry toluene (60 mL) and stirred under reflux for 1 hour. The appropriate salen ligand (1.68 mmol) dissolved in dry toluene (40 mL) was then added and the reaction mixture was stirred under reflux for a further 3 hours before being allowed to cool to room temperature. The solution was dried ($Na_2SO_4$) and solvents were evaporated in vacuo to give a solid which was purified as specified below. The analysis data are set out below.

Data for complex 1a: Yellow solid purified by washing with cold hexane. Yield 63%;
$[\alpha]_D^{20}$ −548 (c=0.11, $CHCl_3$); $\nu_{max}$($CH_2Cl_2$) 2953 m, 1626 m, and 1474 $cm^{-1}$ m; $\delta_H$($CDCl_3$) 8.35 (2H, s, CH=N), 8.15 (2H, s, CH=N), 7.52 (4H, d J2.3 Hz, 4×ArH), 7.07 (4H, d J2.3 Hz, 4×ArH), 3.9-3.7 (2H, br m, CHN), 3.2-3.0 (2H, br m, CHN), 2.7-1.8 (16H, m, 2×$(CH_2)_4$), 1.50 (36H, s, 4×$(CH_3)_3$), 1.29 (36H, s, 4×$(CH_3)_3$); m/z (ESI) 1159.7 ($MH^+$), 649.4, 623.4, 603.4, 569.3. Found (ESI) 1159.7106, $C_{72}H_{105}N_4O_5Al_2$ ($MH^+$) requires 1159.7716.

Data for complex 1b: Orange solid purified by washing with $Et_2O$. Yield 63%;
$[\alpha]_D^{20}$ −575 (c=0.1, toluene); $\nu_{max}$(ATR) 2925 w, 1638 m, 1599 m, and 1573 $cm^{-1}$ m; $\delta_H$($CDCl_3$) 8.64 (4H, s, 4×CH=N), 8.36 (4H, s, 4×ArH), 8.02 (4H, s, 4×ArH), 3.7-3.8 (4H, br, CHN), 3.7-2.0 (16H, m, 2×$(CH_2)_4$), 1.55 (36H, s, 4×$(CH_3)_3$); m/z (ESI) 1115.4 ($MH^+$). Found (ESI) 1115.4536 $C_{56}H_{69}N_8O_{13}Al_2$ ($MH^+$) requires 1115.4615.

Data for complex 1c: Yellow solid purified by washing with cold $Et_2O$. Yield 50%;
$\nu_{max}$(ATR) 2950 m, 2866 w, 1628 m, and 1538 $cm^{-1}$ m; $\delta_H$($CDCl_3$) 8.38 (4H, s, 4×CH=N), 7.52 (4H, d J2.5 Hz, 4×ArH), 7.04 (4H, d J2.6 Hz, 4×ArH), 4.2-4.1 (4H, br, $(CH_2)_2$), 3.8-3.7 (4H, br, $(CH_2)_2$), 1.30 (36H, s, 4×$(CH_3)_3$), 1.55 (36H, s, 4×$(CH_3)_3$); m/z (ESI) 1051.7 ($MH^+$), 664.5, 638.5, 549.4, 517.3. Found (ESI) 1051.6721 $C_{64}H_{93}N_4O_5Al_2$ ($MH^+$) requires 1051.6777.

Data for complex 1d: The reaction was heated at reflux overnight and gave an orange powder. Yield 60%;
$\nu_{max}$($CH_2Cl_2$) 2952 m, 2868 m, 1614 s, 1583 s, and 1531 $cm^{-1}$ s; $\delta_H$($CDCl_3$) 8.66 (4H, s, 4×CH=N), 7.43 (4H, d J2.3

Hz, 4×ArH), 7.3-7.2 (4H, m, 4×ArH), 7.2-7.0 (8H, m, 8×ArH), 1.43 (36H, s, 4×(CH$_3$)$_3$), 1.32 (36H, s, 4×(CH$_3$)$_3$); m/z (Maldi) 1147.7 (MH$^+$), 582.3, 540.4. Found (ESI) 1147.6801 C$_{72}$H$_{93}$N$_4$O$_5$Al$_2$ (MH$^+$) requires 1147.6777.

Data for complex 1e: The reaction was heated at reflux overnight and gave a yellow powder which was purified by dissolution in cold Et$_2$O followed by evaporation of solvent in vacuo. Yield 35%;

[α]$_D^{20}$ –753 (c=0.1, CHCl$_3$); ν$_{max}$(ATR) 2937 m, 2838 m, 1606 s, and 1537 cm$^{-1}$ s; δ$_H$(CDCl$_3$) 9.87 (4H, s, 4×CH=N), 7.18 (4H, dd J8.9, 3.0 Hz, 4×ArH), 7.03 (4H, d J3.1 Hz, 4×ArH), 6.97 (4H, d J9.0 Hz, 4×ArH), 3.82 (12H, s, 4×OCH$_3$), 3.8-3.5 (4H, m, 4×CHN), 1.5-1.2 (16H, m 2×(CH$_2$)$_4$); m/z (Maldi) 831.3 (MH$^+$), 789.3, 662.4, 407.1. Found (ESI) 831.3139 C$_{44}$H$_{49}$N$_4$O$_9$Al$_2$ (MH$^+$) requires 831.3130.

Data for complex 1f: The reaction was heated at reflux overnight and gave a yellow powder which was purified by dissolution in cold Et$_2$O followed by evaporation of solvent in vacuo. Yield 33%;

[α]$_D^{20}$ –381 (c=0.1, CHCl$_3$); ν$_{max}$(ATR) 2863 w, 1628 s, 1601 m, and 1537 cm$^{-1}$ m; δ$_H$(CDCl$_3$) 8.27 (4H, s, CH=N), 7.5-7.4 (4H, m, ArH), 7.2-7.1 (4H, m, ArH), 7.0-6.9 (4H, m, ArH), 6.9-6.8 (4H, m, ArH), 3.4-3.3 (4H, m, CHN), 2.0-1.5 (16H, m, 2×(CH$_2$)$_4$); m/z (ESI) (Maldi) 711.3 (MH$^+$), 669.3, 364.1, 347.1. Found (ESI) 711.2708 C$_{40}$H$_{41}$N$_4$O$_5$Al$_2$ (MH$^+$) requires 711.2708.

Data for complex 1g: The reaction was heated at reflux overnight and gave a yellow powder which was purified by dissolution in cold Et$_2$O followed by evaporation of solvent in vacuo and chromatography on Sephadex LH50 using toleune/ethanol (1:1) as eluent. Yield 45%;

[α]$_D^{20}$ –372 (c=2 (0.1, CHCl$_3$); ν$_{max}$(ATR) 2951 m, 1633 s, and 1538 cm$^{-1}$ m; δ$_H$(CDCl$_3$) 8.28 (4H, s, 4×CH=N), 7.29 (4H, dd J8.1, 2.1 Hz, 4×ArH), 7.14 (4H, d J2.7 Hz, 4×ArH), 6.84 (4H, d J8.7 Hz, 4×ArH), 3.4-3.2 (4H, m, 4×CHN), 2.0-1.4 (16H, m 2×(CH$_2$)$_4$), 1.45 (36H, s, 4×C(CH$_3$)$_3$); m/z (Maldi) 935.5 (MH$^+$), 893.6, 847.5, 775.4, 573.4, 459.3. Found (ESI) 935.5223 C$_{56}$H$_{73}$N$_4$O$_5$Al$_2$ (MH$^+$) requires 935.5212.

Data for complex 1h: The reaction was heated at reflux overnight and gave a yellow powder which was purified by dissolution in cold Et$_2$O followed by evaporation of solvent in vacuo and chromatography on Sephadex LH50 using toleune/ethanol (1:1) as eluent. Yield 30%;

[α]$_D^{20}$ –612 (c=0.1, CHCl$_3$); ν$_{max}$ (ATR) 2949 m, 1627 s, and 1552 cm$^{-1}$ m; δ$_H$(CDCl$_3$) 8.26 (4H, s, 4×CH=N), 6.91 (4H, d J3.0 Hz, 4×ArH), 6.49 (4H, d J3.0 Hz, 4×ArH), 3.70 (12H, s, 4×OCH$_3$), 3.4-3.2 (4H, m, 4×CHN), 2.0-1.4 (16H, m 2×(CH$_2$)$_4$), 1.41 (36H, s, 4×C(CH$_3$)$_3$); m/z (Maldi) 1055.6 (MH$^+$), 876.6, 848.5, 519.3, 494.3. Found (ESI) 1055.5602 C$_{60}$H$_{81}$N$_4$O$_9$Al$_2$ (MH$^+$) requires 1055.5634.

Example 2

General Procedure for the Synthesis of Cyclic Carbonates 3a-k

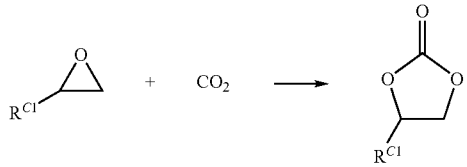

2,3a: R$^{C1}$=Ph
2,3b: R$^{C1}$=Me
2,3c: R$^{C1}$=CH$_2$Ph
2,3d: R$^{C1}$=Bu
2,3e: R$^{C1}$=C$_8$H$_{17}$
2,3f: R$^{C1}$=CH$_2$OH
2,3g: R$^{C1}$=CH$_2$Cl
2,3h: R$^{C1}$=CH$_2$OAc
2,3i: R$^{C1}$=CH$_2$OCOPh
2,3j: R$^{C1}$=CH$_2$OPh
2,3k: R$^{C1}$=

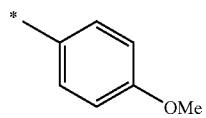

A mixture of an epoxide 2a-k (2 mmol), tetrabutylammonium bromide (0-2.5 mol %) and the appropriate catalyst 1a-h (0-2.5 mol %) was vigorously stirred until complete dissolution occurred, then CO$_2$ was passed through the flask at atmospheric pressure. After being stirred at 25° C. for between 3 and 48 hours, a sample of the reaction was analysed by $^1$H NMR spectroscopy to determine the conversion, and the reaction mixture was purified by flash chromatography to give cyclic carbonate 3a-k. The results are shown below:

| Reaction | Cyclic carbonate | Catalyst (mol %) | Co-catalyst (mol %) | CO$_2$ pressure (atm.) | Temp (° C.) | Time (h) | Conv (%) |
|---|---|---|---|---|---|---|---|
| 1 | 3a | 1a (0.1) | Bu$_4$NBr (0.1) | 1 | 25 | 3 | 5 |
| 2 | 3a | 1a (1.0) | Bu$_4$NBr (1.0) | 1 | 25 | 3 | 38 |
| 3 | 3a | 1a (1.0) | Bu$_4$NBr (2.5) | 1 | 25 | 3 | 56 |
| 4 | 3a | 1a (2.5) | Bu$_4$NBr (1.0) | 1 | 25 | 3 | 51 |
| 5 | 3a | 1a (2.5) | Bu$_4$NBr (2.5) | 1 | 25 | 3 | 62 |
| 6 | 3a | 1a (0.1) | Bu$_4$NBr (0.1) | 1 | 25 | 24 | 27 |
| 7 | 3a | 1a (1.0) | Bu$_4$NBr (1.0) | 1 | 25 | 24 | 86 |
| 8 | 3a | 1a (2.5) | Bu$_4$NBr (2.5) | 1 | 25 | 24 | 98 |
| 9 | 3a | 1b (2.5) | Bu$_4$NBr (2.5) | 1 | 25 | 3 | 50 |
| 10 | 3a | 1c (2.5) | Bu$_4$NBr (2.5) | 1 | 25 | 3 | 52 |
| 11 | 3a | 1d (2.5) | Bu$_4$NBr (2.5) | 1 | 25 | 3 | 33 |
| 12 | 3a | 1e (2.5) | Bu$_4$NBr (2.5) | 1 | 25 | 3 | 41 |
| 13 | 3a | 1f (2.5) | Bu$_4$NBr (2.5) | 1 | 25 | 3 | 28 |
| 14 | 3a | 1g (2.5) | Bu$_4$NBr (2.5) | 1 | 25 | 3 | 51 |
| 15 | 3a | 1h (2.5) | Bu$_4$NBr (2.5) | 1 | 25 | 3 | 64 |
| 16 | 3b | 1a (2.5) | Bu$_4$NBr (2.5) | 1 | 25 | 3 | 77 |
| 17 | 3b | 1a (1) | Bu$_4$NBr (1) | 1 | 0 | 3 | 40 |

| Reaction | Cyclic carbonate | Catalyst (mol %) | Co-catalyst (mol %) | $CO_2$ pressure (atm.) | Temp (° C.) | Time (h) | Conv (%) |
|---|---|---|---|---|---|---|---|
| 18 | 3b | 1a (1) | $Bu_4NBr$ (1) | 1 | 0 | 24 | 63 |
| 19 | 3c | 1a (2.5) | $Bu_4NBr$ (2.5) | 1 | 0 | 3 | 44 |
| 20 | 3c | 1a (2.5) | $Bu_4NBr$ (2.5) | 1 | 25 | 24 | 99 |
| 21 | 3d | 1a (2.5) | $Bu_4NBr$ (2.5) | 1 | 25 | 3 | 87 |
| 22 | 3e | 1a (2.5) | $Bu_4NBr$ (2.5) | 1 | 25 | 3 | 64 |
| 23 | 3f | 1a (2.5) | $Bu_4NBr$ (2.5) | 1 | 25 | 3 | 43 |
| 24 | 3g | 1a (2.5) | $Bu_4NBr$ (2.5) | 1 | 25 | 3 | 90 |
| 25 | 3h | 1a (2.5) | $Bu_4NBr$ (2.5) | 1 | 25 | 3 | 50 |
| 26 | 3h | 1a (2.5) | $Bu_4NBr$ (2.5) | 1 | 25 | 24 | 75 |
| 27 | 3i | 1a (2.5) | $Bu_4NBr$ (2.5) | 1 | 25 | 3 | 72 |
| 28 | 3i | 1a (2.5) | $Bu_4NBr$ (2.5) | 1 | 25 | 24 | 62 |
| 29 | 3j | 1a (2.5) | $Bu_4NBr$ (2.5) | 1 | 25 | 3 | 55 |
| 30 | 3k | 1a (2.5) | $Bu_4NBr$ (2.5) | 1 | 25 | 3 | 30 |
| 31 | 3k | 1a (2.5) | $Bu_4NBr$ (2.5) | 1 | 25 | 24 | 84 |
| Comparative reaction 1 | 3a | 1a (1.0) | — | 1 | 25 | 3 | 0 |
| Comparative reaction 2 | 3a | 1a (1.0) | — | 5 | 50 | 24 | 0 |
| Comparative reaction 3 | 3a | 1a (0.1) | DMAP (1.0) | 8 | 50 | 24 | 0 |
| Comparative reaction 4 | 3a | — | $Bu_4NBr$ (1.0) | 1 | 25 | 3 | 4 |

Detailed Results for Example 2
The analysis data are given below for cyclic carbonates 3a-e, synthesised under the following conditions:
Temperature: 25° C.
Pressure: atmospheric
Reaction time: 3 hours
Catalyst: 1a (2.5 mol %)
Co-catalyst: $Bu_4NBr$ (2.5 mol %)

Data for styrene carbonate 3a—Reaction 5: Conversion 62%, isolated yield 57% after purification by flash chromatography (hexane/EtOAc 2:3). Mp 49-52° C.; $v_{max}$ (ATR) 3047 m, 3020 m, 2968 m, 2899 m, 1812 s, and 1592 $cm^{-1}$ w; $\delta_H$ 7.5-7.2 (5H, m, ArH), 5.68 (1H, t J8.0 Hz, PhCHO), 4.81 (1H, t J8.5 Hz, $OCH_2$), 4.35 (1H, t J8.4 Hz, $OCH_2$). $\delta_C$ 154.9, 135.9, 129.8, 129.3, 126.0, 78.1, 71.3; m/z (EI) 164 ($M^+$, 100), 119 (10), 105 (10).

Data for propylene carbonate 3b—Reaction 17: Reaction carried out at 0° C., conversion 82%, isolated yield 77% after purification by flash chromatography (hexane/EtOAc) $v_{max}$ (neat) 2991 m, 2921 m, 1786 $cm^{-1}$ s; $\delta_H$ 4.9-4.8 (1H, m, CHO), 4.55 (1H, t J8.4 Hz $OCH_2$), 4.02 (1H, dd J8.4, 7.3 Hz $OCH_2$), 1.49 (3H, d J6.3 Hz, $CH_3$); $\delta_C$ 154.5, 73.7, 70.9, 19.7; m/z (EI) 102 ($M^+$, 100), 100 (5).

Data for allylbenzene carbonate 3c—Reaction 19: Conversion 50%, isolated yield 44% after purification by flash chromatography (hexane/EtOAc 2:3). $v_{max}$ (neat) 3064 w, 3031 w, 2980 w, 2920 w, 1800 $cm^{-1}$ s; $\delta_H$ 7.2-7.0 (5H, m, ArH), 4.85 (1H, m, OCH), 4.35 (1H, t J7.8 Hz, $OCH_2$), 4.08 (1H, dd J8.4, 6.9 Hz, $OCH_2$), 3.06 (1H, dd J14.1, 6.3 Hz, $CH_2Ph$), 2.90 (1H, dd J14.1, 6.3 Hz, $CH_2Ph$); $\delta_C$ 154.5, 134.1, 129.3, 128.9, 127.5, 76.8, 68.5, 39.6; m/z (EI), 178 ($M^+$, 20), 91 (100).

Data for hex-1-ene carbonate 3d—Reaction 21: Conversion 90%, isolated yield 87% after purification by flash chromatography (hexane/EtOAc 2:3). $v_{max}$ (neat) 2960 s, 2934 s, 2874 m, 1797 $cm^{-1}$ s; $\delta_H$ 4.64 (1H, qd J7.5, 5.4 Hz, OCH), 4.46 (1H, t J7.8 Hz, $OCH_2$), 4.09 (1H, dd J8.4, 7.2 Hz, $OCH_2$), 2.0-1.6 (2H, m, $CH_2$), 1.6-1.2 (4H, m, 2×$CH_2$), 0.95 (3H, t J7.1 Hz, $CH_3$); $\delta_C$ 155.2, 77.2, 69.5, 33.7, 26.5, 22.4, 13.9; m/z? ($C_1$, $NH_3$), 162 ($M+NH_4^+$, 100), 161 (40), 100 (10).

Data for dec-1-ene carbonate 3e—Reaction 22: Conversion 70%, isolated yield 64% after purification by flash chromatography ($Et_2O$). $v_{max}$ (neat) 2928 s, 2857 s, 1805 $cm^{-1}$ s; $\delta_H$ 4.72 (1H, qd J7.5, 5.7 Hz, OCH), 4.54 (1H, t J8.1 Hz, $OCH_2$), 4.09 (1H, t J7.5 Hz, $OCH_2$), 1.9-1.6 (2H, m, $CH_2$), 1.6-1.2 (12H, m, 6×$CH_2$), 0.90 (3H, t J6.6 Hz, $CH_3$); $\delta_C$ 155.2, 77.1, 69.5, 34.0, 31.9, 29.4, 29.2, 29.1, 24.5, 22.7, 14.2; m/z (EI), 162 ($M^+$, 8), 95 (38), 67 (100).

Data for hydroxypropyl carbonate 3f—Reaction 23: Conversion 43%, isolated yield 36% after purification by distillation. $v_{max}$ (neat) 3400 s, 2933 m, and 1789 $cm^{-1}$ s; $\delta_H$($CDCl_3$) 4.8-4.9 (1H, m, OCH), 4.4-4.5 (2H, m, $CH_2$), 3.9-4.0 (1H, m OCH), 3.6-3.8 (2H, br, OH, OCH); $\delta_C$($CDCl_3$) 155.2, 75.0, 65.8, 61.6; m/z (CI) 119 ($MH^+$, 100), 118 ($M^+$, 10).

Data for chloropropyl carbonate 3g—Reaction 24: Conversion 90%, isolated yield 60% after purification by flash chromatography (hexane/EtOAc 2:3). $v_{max}$(neat) 3467 w, 1960 m, and 1799 $cm^{-1}$ s; $\delta_H$($CDCl_3$) 5.0-4.9 (1H, m, OCH), 4.59 (1H, dd J8.7, 8.4 Hz, $OCH_2$), 4.40 (1H, dd J9.0, 8.7 Hz, $OCH_2$), 3.8-3.7 (2H, m, $CH_2Cl$); $\delta_C$ ($CDCl_3$) 154.4, 74.6, 67.4, 43.9; m/z (EI) 139 (($^{37}Cl$)$M^+$, 5), 137 (($^{35}Cl$)$M^+$, 10), 86 (35), 87 (55), 49 (45), 51 (13), 43 (100), 44 (25).

Data for acetyloxypropyl carbonate 3h—Reaction 25: Conversion 50%, isolated yield 34% after purification by flash chromatography (hexane/EtOAc 2:3). Reaction 26: Conversion 75%, isolated yield 55% after purification by flash chromatography. $v_{max}$ (neat) 3545 m, 2960 m, 1788 s, and 1746 $cm^{-1}$ s; $\delta_H$($CDCl_3$) 4.93 (1H, m, OCH), 4.57 (1H, t J9.0 Hz, $OCH_2$), 4.27 (3H, m, $OCH_2$, $CH_2$), 2.15 (3H, s, $CH_3$); $\delta_C$($CDCl_3$) 170.5, 154.8, 74.1, 66.4, 63.4, 20.1; m/z (EI) 161 ($MH^+$, 75) 160 ($M^+$, 8), 43 (100).

Data for phenylcarbonyloxypropyl carbonate 3i—Reaction 27: Conversion 72%, isolated yield 12% after purification by flash chromatography (hexane/EtOAc 1:3). Reaction 28: Conversion 62%, isolated yield 58% following purification by flash chromatography (hexane/EtOAc 1:3). $v_{max}$ (neat) 3585 m, 3055 m, 2956 m, 1799 s, and 1715 $cm^{-1}$ s; $\delta_H$($CDCl_3$) 8.0-8.1 (2H, m, ArH) 7.6-7.7 (1H, m, ArH), 7.4-7.5 (2H, m, ArH), 5.0-5.1 (1H, m, OCH), 4.5-4.6 (4H, m, $OCH_2$, $CH_2$); $\delta_C$ ($CDCl_3$) 166.4, 154.8, 134.1, 130.2, 129.2, 129.1, 74.3, 66.5, 66.0; m/z (EI) 223 ($MH^+$, 3), 122 (13), 105 (100), 77 (38), 51 (15).

Data for phenoxypropylcarbonate 3j—Reaction 29: Conversion 55%, isolated yield 46% following purification by flash chromatography (hexane/EtOAc 2:3) followed by recrystallization from hexane. $v_{max}$(neat) 2524 w, 2160 s, 2032 s, 1976 s, and 1783 cm$^{-1}$ s; $\delta_H$(CDCl$_3$) 7.3-7.4 (2H, m, 2×ArH), 7.01 (1H, t J7.4 Hz, ArH), 6.9-7.0 (2H, m, 2×ArH), 5.1-5.0 (1H, m, OCH), 4.7-4.5 (2H, m, OCH$_2$), 4.24 (1H, dd J10.5, 4.2 Hz, OCH$_2$), 4.14 (1H, dd J 10.8, 9.0 Hz, OCH$_2$); $\delta_C$ (CDCl$_3$) 158.1, 155.0, 130.1, 122.4, 155.0, 74.5, 67.3, 66.6; m/z (EI) 194 (M$^+$, 100), 133 (11), 107 (70), 94 (50), 79 (25), 66 (18).

Data for 4-methoxyphenylethylcarbonate 3k—reaction 30: Yield 30%. Reaction 31: yield 84%, isolated yield 79% following purification by flash chromatography (hexane/EtOAc 2:3). $v_{max}$ (neat) 2926 w, 1789 s, 1612 s, 1513 s, 1248 s, and 1163 cm$^{-1}$ s; $\delta_H$(CDCl$_3$) 7.29 (2H, d J8.7 Hz, 2×ArH), 6.94 (2H, d J8.7 Hz, 2×ArH), 5.60 (1H, t J8.1 Hz, OCH), 4.74 (1H, t J8.4 Hz, OCH$_2$), 4.33 (1H, t J9.0 Hz, OCH$_2$), 3.81 (3H, s, OCH$_3$); $\delta_C$(CDCl$_3$) 160.7, 154.8, 127.7, 127.4, 114.6, 78.1, 71.0, 55.3; m/z (EI) 195 (MH$^+$, 12), 194 (M$^+$, 20), 150 (50), 149 (25), 135 (20), 122 (12), 121 (100), 119 (20), 91 (25).

Example 3

1R,2R)-Cyclohexane-1,2-diammonium dichloride
(5)

(Larrow, J. F, et al., *J. Org. Chem.* 1994, 59, 193

To a suspension of (1R,2R)-cyclohexane-1,2-diammonium L-tartrate (4)(13.7 g, 52 mmol) in MeOH (50 mL) was added a cooled solution (0° C.) of acetyl chloride (27.4 mL, 385 mmol) in MeOH (50 mL). The solution was stirred at room temperature overnight. The resulting precipitate was filtered off, washed with Et$_2$O (10 mL) and dried by suction to leave the desired product as a white powder. A second crop was obtained by diluting the mother liquor with Et$_2$O (200 mL) and cooling for half an hour. The product was collected and dried to yield a white powder. Yield: 80%. Crystalline white powder. $[\alpha]^{20}_D$ −16 (c 5.0, aq. 1 M HCl). $^1$H-NMR $\delta_H$ (DMSO-d$_6$, 300 MHz): 1.05-1.25, 1.30-1.55 (4H, 2m, CH$_2$CH$_2$CHN), 1.60-1.75, 2.00-2.15 (4H, 2m, CH$_2$CHN), 3.13-3.30 (2H, m, CHN), 8.70 (6H, br s, NH$_3$).

3-tert-Butylsalicylaldehyde (7)

(Gisch, N.; Balzarini, J.; Meier, C. *J. Med. Chem.* 2007, 50, 1658)

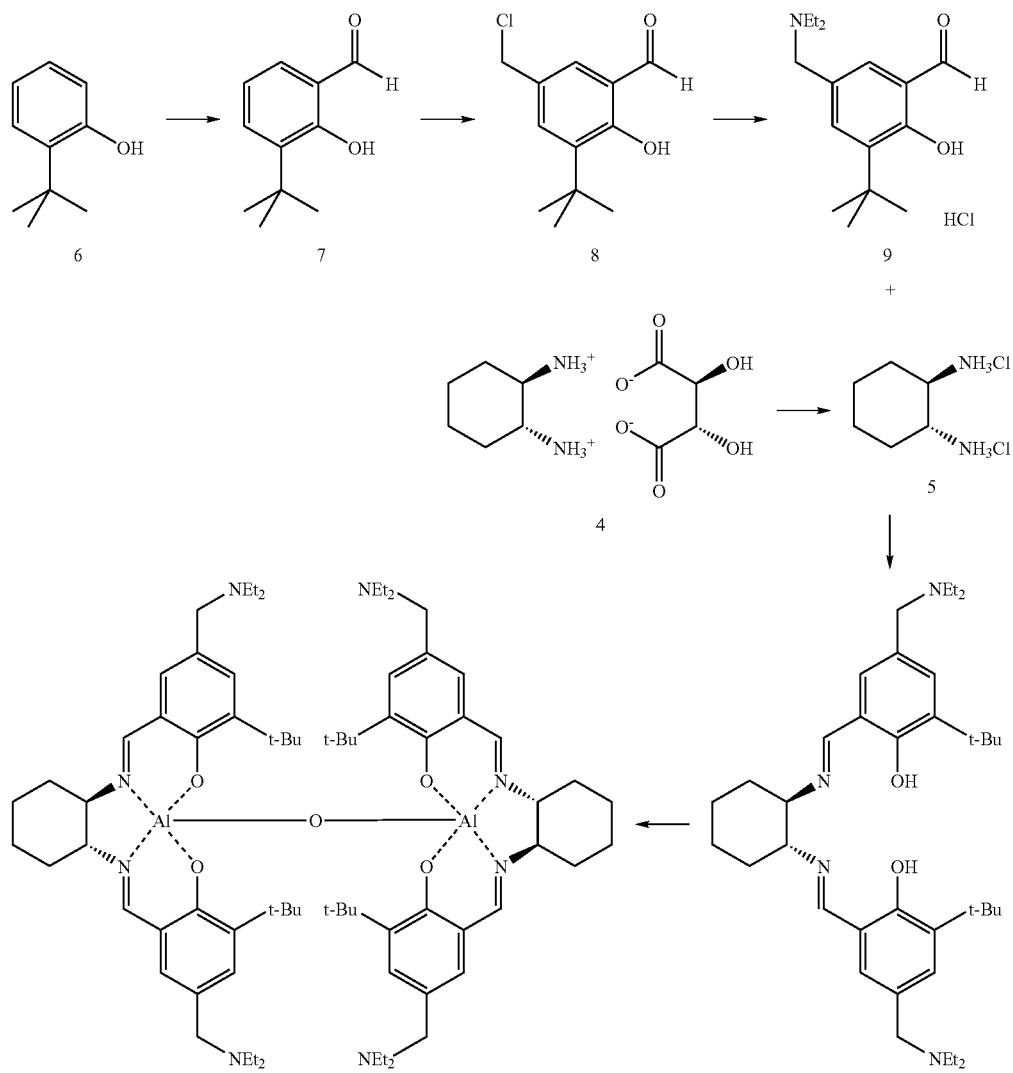

To a stirred suspension of 2-tert-butylphenol (6)(4.55 g, 30 mmol), magnesium chloride (5.71 g, 60 mmol) and paraformaldehyde (2.08 g, 66 mmol) in THF (120 mL) at room temperature, was added triethylamine (8.35 mL, 60 mmol) dropwise. The reaction was heated to reflux for 3 hours to give an orange suspension. The crude was extracted using EtOAc (3×50 mL). A small amount of diluted HCl can be added if a permanent emulsion is formed. The organic layers were dried over MgSO$_4$ and the volatiles evaporated under low pressure to yield a pale yellow oil which did not need any further purification. It can become dark green on storage. Yield: 90%. Pale yellow oil. $^1$H-NMR $\delta_H$ (CDCl$_3$, 300 MHz): 1.44 (9H, s, 3×CH$_3$), 6.97 (1H, t, J=7.5 Hz, H$_{Ar}$), 7.41 (1H, dd, J=1.5 Hz, J=7.5 Hz, H$_{Ar}$), 7.54 (1H, dd, J=1.2 Hz, J=7.5 Hz, H$_{Ar}$), 9.88 (1H, s, CHO), 11.82 (1H, s, OH).

3-tert-Butyl-5-chloromethylsalicylaldehyde (8)

A mixture of 3-tert-butylsalicylaldehyde (7)(3.56 g, 20 mmol) and paraformaldehyde (1.20 g, 40 mmol) was stirred with concentrated HCl (15 mL) for 14 days, although with the first drops of concentrated HCl, the emulsion became red. The mixture was then treated with a saturated solution of Na$_2$CO$_3$ until neutralisation. The mixture was extracted with EtOAc (3×30 mL). Organic layers were dried over MgSO$_4$ and the volatiles were evaporated under low pressure to give a beige solid which did not require further purification. Yield: 97%. Beige to red solid. $^1$H-NMR $\delta_H$ (CDCl$_3$, 300 MHz): 1.43 (9H, s, 3×CH$_3$), 4.59 (2H, s, CH$_2$), 7.43, 7.52 (2H, 2d, J=2.1 Hz, 2×H$_{Ar}$), 9.87 (1H, s, CHO), 11.86 (1H, s, OH).

3-tert-Butyl-5-diethylaminomethylsalicylaldehyde hydrochloride (9)

To a solution of 3-tert-butyl-5-chloromethylsalicylaldehyde (8)(226.5 mg, 1 mmol) in acetonitrile (60 mL), diethylamine (1 mmol) was added dropwise to give a greenish solution. The reaction was stirred at 30° C. overnight. After evaporation of volatiles, a green oil was obtained and it was used without any purification for the next step. Yield: 77%. Green oil. IR 3300, 2899, 1720. $^1$H-NMR $\delta_H$ (CDCl$_3$, 300 MHz): 1.35 (9H, s, C(CH$_3$)$_3$), 1.45 (61-1, t, J=7.2 Hz, 2×CH$_2$CH$_3$), 3.43 (4H, q, J=7.2 Hz, 2×CH$_2$CH$_3$), 4.90 (2H, s, CCH$_2$N), 7.57, 8.03 (2H, 2d, J=2.1 Hz, 2×HAr), 9.98 (1H, s, CHO), 12.00 (1H, br s, OH). $\delta_C$(CDCl$_3$, 75 MHz): 10.8, 28.3, 33.7, 45.8, 56.0, 119.5, 129.8, 130.3, 133.7, 137.0, 159.0, 195.9.

HRMS: Calcd. for C$_{18}$H$_{30}$NO$_2$$^+$ 292.2277. found 292.2243.

(1R,2R)—N,N'-Bis(3-tert-butyl-5-diethylaminomethylsalicylidene)cyclohexane-1,2-diamine (10)

(1R,2R)-cyclohexane-1,2-diammonium dichloride (5)(93.5 mg, 0.5 mmol) and NaOMe (55 mg, 1 mmol) were stirred in MeOH (10 mL) for 30 min. After that, a solution of 3-tert-butyl-5-diethylaminomethylsalicylaldehyde hydrochloride (9)(299.8 mg, 1 mmol) in MeOH (5 mL) was added and the solution, which became rapidly yellow, was stirred overnight at 30° C. Evaporation of MeOH was followed by addition of a saturated solution of Na$_2$CO$_3$ (20 mL). Organic compounds were extracted using dichloromethane (3×15 mL). It is important that the aqueous phase remains completely colourless and the organic layer changes from orange to green colour. Organic layers were dried over MgSO$_4$ and volatiles were removed under vacuum to give a greenish slurry oil which was used without any purification in the next step. Yield: 55%. Yellow-green oil. $[\alpha]^{20}_D$ −184.5 (c 1.0, CHCl$_3$). IR 3410, 2899, 1610, 1550, 830. $^1$H-NMR $\delta_H$ (CDCl$_3$, 300 MHz): 0.99 (12H, t, J=7.2 Hz, 4×CH$_2$CH$_3$), 1.40 (18H, s, 2×C(CH$_3$)$_3$), 1.50-2.05 (8H, m, (CH$_2$)$_4$), 2.44 (8H, q, J=7.2 Hz, 4×CH$_2$CH$_3$), 3.40-3.50 (6H, m, 2×CHN, 2×CCH$_2$N), 6.95, 7.17 (4H, 2d, J=1.8 Hz, 4×H$_{Ar}$), 8.28 (2H, s, 2×HC=N), 13.77 (2H, br s, 2×OH). $\delta_C$(CDCl$_3$, 75 MHz): 11.9, 24.4, 29.6, 33.2, 34.8, 46.8, 57.3, 72.5, 118.4, 128.8, 129.8, 130.1, 136.9, 159.3, 165.7. HRMS: Calcd. for C$_{38}$H$_{61}$N$_4$O$_2$$^+$ 605.4795. found 605.4783.

Bis[(1R,2R)—N,N'-Bis(3-tert-butyl-5-diethylaminomethylsalicylidene)cyclohexane-1,2-diaminoaluminium(III)]oxide (11)

This reaction was performed under an inert atmosphere in dry conditions. The ligand (10)(1 mmol) and Al(OEt)$_3$ (324.1 mg, 2 mmol) were dissolved in toluene (10 mL). The reacting mixture was heated to reflux for 5 hours. Occasional residue of alumina could be removed by filtering through a sinter. The mother liquor was evaporated and then, H$_2$O (30 mL) and CH$_2$Cl$_2$(30 mL) were added. The complex was extracted using dichloromethane (3×20 mL) and organic layers were dried over MgSO$_4$. Volatiles were removed under low pressure to give a pale solid, which was recrystallised using acetonitrile. Yield: 40%. Pale green solid. $[\alpha]^{20}_D$ −522 (c 1.0, CHCl$_3$). IR 2865, 1626, 1548, 1440, 1027, 836, 577. $^1$H-NMR $\delta_H$ (CDCl$_3$, 300 MHz): 1.02 (24H, t, J=7.2 Hz, 8×CH$_2$CH$_3$), 1.46 (36H, s, 4×C(CH$_3$)$_3$), 1.50-2.15 (16H, m, 2×(CH$_2$)$_4$), 2.52 (16H, m, 8×CH$_2$CH$_3$), 3.10-3.15, 3.80-3.85 (4H, 2m, 4×CHN), 3.50 (8H, m, 4×CCH$_2$N), 7.09, 7.35 (8H, 2d, J=5.7 Hz, 8×H$_{Ar}$), 8.19, 8.37 (4H, 2s, 4×HC=N). ($\delta_C$ (CDCl$_3$, 75 MHz): 10.2, 24.7, 29.9, 30.1, 35.0, 47.1, 57.6, 73.2, 118.9, 119.2, 128.9, 135.3, 141.7, 157.2, 165.1. m/z (electrospray) 661.5 (100), 1275.9 (80), 1276.9 (72), 1277.9 (32), 1278.9 (16), 1279.9 (4)

Use of Catalyst 11

Catalyst 11 was tested in the insertion of carbon dioxide into styrene oxide. The reaction was carried out with no solvent using catalyst 11 (2.5 mol %) and tetrabutylammonium bromide (2.5 mol %) under a carbon dioxide atmosphere (1 atm. Pressure). After 3 hours a conversion of 69% was obtained.

Example 4

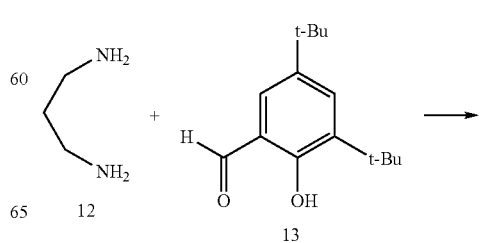

-continued

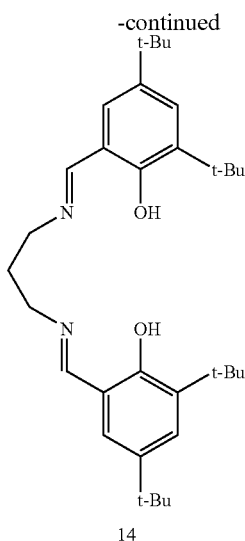

14

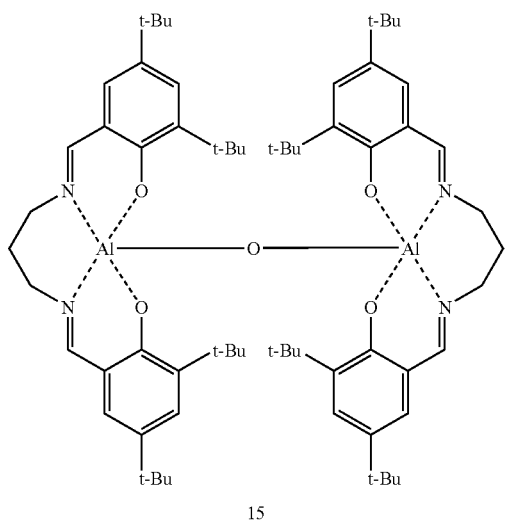

15

N,N'-bis(3,5-di-tert-butyl-salicylidene)propane-1,3-diamine (14)

(Nomura, N. et al., *Chem. Eur. J.* 2007, 13, 4433-4451)

3,5-Di-tert-butyl salicylaldehyde (13)(1.34 mmol) and 1,3-diamino propane (12)(0.68 mmol) were mixed together and stirred at room temperature. After 1 hour, methanol (4 mL) was added forming a yellow precipitate which was allowed to stir overnight. The precipitate was extracted with $CH_2Cl_2$/water (2×10 mL of $CH_2Cl_2$), then the organic layer was recovered, dried ($Na_2SO_4$) and finally evaporated under vacuum to give a yellow residue which was recrystallized from methanol to give the desired ligand (96%) as a yellow solid. $v_{max}$ (ATR) 2956 s, 2530 w, 2159 s, 2031 s, 1977 s, 1630 s, and 1439 $cm^{-1}$ m; $\delta_H$(CDCl$_3$) 13.82 (2H, s, 2×OH), 8.39 (2H, s, 2×CH=N), 7.39 (2H, d J2.4 Hz, ArH), 7.09 (2H, d J2.4 Hz, ArH), 3.71 (4H, t J6.4 Hz, 2×CH$_2$), 2.1-2.2 (2H, m, —CH$_2$—); $\delta_C$(CDCl$_3$, 75 MHz): 166.5, 158.1, 140.1, 136.7, 126.7, 125.8, 56.8, 35.0, 34.1, 31.5, 29.5, 26.2; HRMS: Calcd. for $C_{33}H_{51}N_2O_2$ (MH$^+$) 507.3988. found 507.3951.

Catalyst 15

N,N'-bis(3,5-di-tert-butyl-salicylidene)propane-1,3-diamine (14)(0.19 mmol) and Al(OEt)$_3$ (0.20 mmol) were dissolved in toluene (40 mL) and heated at reflux for 4 hours. Solvents were removed under reduced pressure and $H_2O$ (20 mL) and $CH_2Cl_2$ (20 mL) were added. The complex was extracted using dichloromethane (3×20 mL) and the organic layers were combined and dried (MgSO$_4$). Solvents were removed under reduced pressure to give the desired complex as a yellow solid in 45% yield. $v_{max}$ (ATR) 2959 m, and 1622 $cm^{-1}$ m; $\delta^H$(CDCl$_3$) 1.31 (36H, s, 4×C(CH$_3$)$_3$), 1.46 (36H, s, 4×C(CH$_3$)$_3$), 2.1-2.2 (4H, m, 2×CH$_2$), 3.71 (8H, t J6.9 Hz, 4×NCH$_2$), 7.09 (4H, d J2.4 Hz, 4×ArH), 7.39 (4H, d J2.4 Hz, 4×ArH), 8.40 (4H, s, 4×CH=N); m/z found (ESI) 1079.7168 $C_{66}H_{97}N_4O_5Al_2$ (MH$^+$) requires 1079.7090.

Use of Catalyst 15

Catalyst 15 was tested in the insertion of carbon dioxide into styrene oxide. The reaction was carried out with no solvent using catalyst 15 (2.5 mol %) and tetrabutylammonium bromide (2.5 mol %) under a carbon dioxide atmosphere (1 atm. Pressure). After 3 hours a conversion of 14% was obtained.

What is claimed is:

1. A process for the production of cyclic carbonates comprising contacting an epoxide with carbon dioxide in the presence of a dimeric aluminium(salen) catalyst, and a co-catalyst capable of supplying where Y is selected from Cl, Br and I, and the co-catalyst is selected from the group consisting of NaCl, KI, R$_4$NY, R$_3$SY, R$_4$PY and R$_4$SbY, where each R is independently selected from $C_{1-10}$ alkyl, where the dimeric aluminium(salen) catalyst is of formula I:

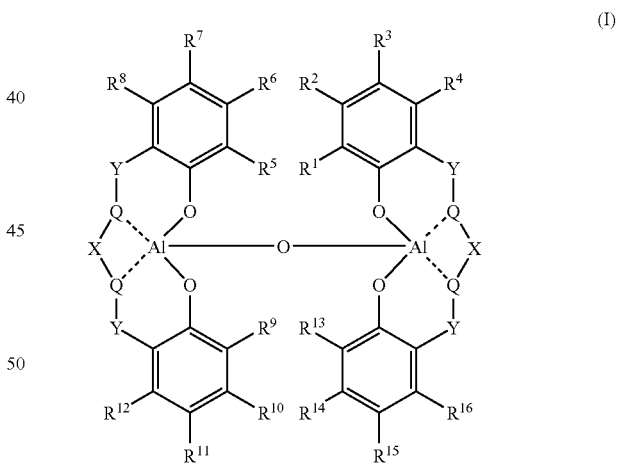

(I)

wherein:

Y-Q is CH=N each of the substituents R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, and R$^{16}$, is independently selected from H, $C_{1-7}$ alkyl, $OC_{1-7}$ alkyl, and nitro; or R$^4$=R$^8$=R$^{12}$=R$^{16}$=H, and R$^1$, R$^2$, R$^3$, R$^5$, R$^6$, R$^7$, R$^9$, R$^{10}$, R$^{11}$, R$^{13}$, R$^{14}$, and R$^{15}$ are independently selected from H, $C_{1-7}$ alkyl, and diethylaminomethyl;

X is the formula —(CH$_2$)$_n$—, where n is 2, or 3, or represents a divalent group selected from $C_6$arylene, and $C_6$cyclic alkylene.

2. The process of claim 1, wherein the catalysed reaction is:

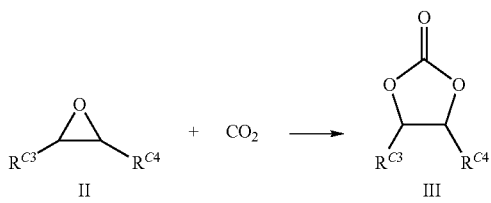

wherein $R^{C3}$ and $R^{C4}$ are independently selected from H, optionally substituted $C_{1-10}$ alkyl, optionally substituted $C_{3-20}$ heterocyclyl and optionally substituted $C_{5-20}$ aryl, or $R^{C3}$ and $R^{C4}$ form an optionally substituted linking group between the two carbon atoms to which they are respectively attached.

3. The process according to claim 1, wherein the source of $Y^-$ is selected from $R_4NY$, $R_3SY$, $R_4PY$ and $R_4SbY$, where each R is independently selected from $C_{1-10}$ alkyl.

4. The process according to claim 1, wherein the aluminium(salen) catalyst of formula I is symmetrical, such that $R^1=R^{13}$, $R^2=R^{14}$, $R^3=R^{15}$, $R^4=R^{16}$, $R^5=R^9$, $R^6=R^{10}$, $R^7=R^{11}$, and $R^8=R^{12}$.

5. The process according to claim 4, wherein $R^1$, $R^5$, $R^9$, and $R^{13}$ are identical, $R^2$, $R^6$, $R^{10}$ and $R^{14}$ are identical, $R^3$, $R^7$, $R^{11}$, and $R^{15}$ are identical, and $R^4$, $R^8$, $R^{12}$ and $R^{16}$ are identical.

6. The process according to claim 1, wherein X represents a divalent group selected from $C_6$arylene and $C_6$cyclic alkylene.

7. The process according to claim 1, wherein $R^4=R^8=R^{12}=R^{16}=H$.

* * * * *

UNITED STATES PATENT AND TRADEMARK OFFICE
CERTIFICATE OF CORRECTION

| | | |
|---|---|---|
| PATENT NO. | : 9,242,955 B2 | Page 1 of 1 |
| APPLICATION NO. | : 12/597417 | |
| DATED | : January 26, 2016 | |
| INVENTOR(S) | : Michael North | |

It is certified that error appears in the above-identified patent and that said Letters Patent is hereby corrected as shown below:

Specification

Column 25, In line 65, after ";" delete "δ"

Claims

Column 26, In line 30, claim 1, after "supplying" insert -- $Y^-$, --

Signed and Sealed this
Twenty-sixth Day of April, 2016

Michelle K. Lee
*Director of the United States Patent and Trademark Office*